(12) United States Patent
Birge et al.

(10) Patent No.: US 8,883,719 B2
(45) Date of Patent: Nov. 11, 2014

(54) BACTERIORHODOPSIN PROTEIN VARIANTS AND METHODS OF USE FOR LONG TERM DATA STORAGE

(75) Inventors: Robert R. Birge, Coventry, CT (US); Rekha Rangarajan, Fort Worth, TX (US); Kristina Nicole McCleary, Cheshire, CT (US)

(73) Assignee: University of Connecticut, Farmington, CT (US)

( * ) Notice: Subject to any disclaimer, the term of this patent is extended or adjusted under 35 U.S.C. 154(b) by 907 days.

(21) Appl. No.: 12/353,282

(22) Filed: Jan. 14, 2009

(65) Prior Publication Data

US 2009/0268511 A1     Oct. 29, 2009

Related U.S. Application Data

(60) Provisional application No. 61/021,477, filed on Jan. 16, 2008.

(51) Int. Cl.
| | |
|---|---|
| *C07K 14/00* | (2006.01) |
| *G11C 13/04* | (2006.01) |
| *B82Y 10/00* | (2011.01) |
| *C07K 14/195* | (2006.01) |
| *G11C 13/00* | (2006.01) |

(52) U.S. Cl.
CPC .............. *G11C 13/04* (2013.01); *G11C 13/044* (2013.01); *B82Y 10/00* (2013.01); *C07K 14/195* (2013.01); *G11C 13/0014* (2013.01); *G11C 13/0019* (2013.01); *G11C 13/047* (2013.01)
USPC ............................................. 514/2; 530/300

(58) Field of Classification Search
None
See application file for complete search history.

(56) References Cited

U.S. PATENT DOCUMENTS

| | | | |
|---|---|---|---|
| 5,253,198 | A | 10/1993 | Birge et al. |
| 5,268,862 | A | 12/1993 | Rentzepis |
| 5,559,732 | A | 9/1996 | Birge |
| 7,109,136 | B2 | 9/2006 | Senecal et al. |
| 7,135,261 | B2 | 11/2006 | Yamazaki et al. |
| 7,291,540 | B2 | 11/2007 | Mech et al. |
| 7,939,220 | B2 * | 5/2011 | Oesterhelt et al. ............. 430/1 |
| 8,563,026 | B2 | 10/2013 | Birge et al. |
| 2006/0009805 | A1 | 1/2006 | Jensen et al. |
| 2006/0187795 | A1 | 8/2006 | Redfield et al. |
| 2009/0032683 | A1 | 2/2009 | Knopf et al. |
| 2009/0229669 | A1 | 9/2009 | Birge et al. |
| 2010/0226957 | A1 | 9/2010 | Birge et al. |
| 2010/0229384 | A1 | 9/2010 | Krulevitch et al. |

FOREIGN PATENT DOCUMENTS

| | | |
|---|---|---|
| WO | 2008141271 | 11/2008 |
| WO | 2010102205 A2 | 9/2010 |
| WO | 2010102205 | 2/2011 |

OTHER PUBLICATIONS

NCBI Reference Sequence ZP_01253360.1 (Downloaded from website on Aug. 10, 2011). First seen on NCBI on Apr. 7, 2006.*
NCBI Reference Sequence ZP_01253360. First seen on NCBI on Apr. 7, 2006 documentation in PDF format.*
Bowie, James U. et al., "Deciphering the Message in Protein Sequences: Tolerance to Amino Acid Substitutions", Science Mar. 16, 1990, vol. 247, 1306-1310.
Greener, Alan et al., "An Efficient Random Mutagenesis Technique Using an *E. coli* Mutator Strain", Methods in Molecular Biology 1996 , vol. 57; pp. 375-385.
Krebs, Mark P. "Gene replacement in *Halobacterium halobium* and expression of bacteriorhodopsin mutants", Proc. Natl. Acad. Sci. USA Mar. 1993 , vol. 90, 1987-1991.
Krebs, Mark P. "Intramembrane Substitutions in Helix D of Bacteriorhodopsin Disrupt the Purple Membrane", J. Mol. Biol. 1997 , vol. 267; 172-183.
Peck, Ronald F. et al., "Homologous gene knockout in the archaeon *Halobacterium salinarum* with ura3 as a counterselectable marker", Molecular Microbiology 2000, 35(3); 667-776.
Wan, Lianglu et al., "In vitro evolution of horse heart myoglobin to increase peroxidase activity", Proc. Natl. Acad. Sci. USA Oct. 1998, vol. 95; 12825-12831.
Wen, Juan et al., "Exploring the allowed sequence space of a membrane protein", Nature Structural Biology Feb. 1996, vol. 3, No. 2; 141-148.
Whaley, Sandra R. et al., "Selection of peptides with semiconductor binding specificity for directed nanocrystal assembly", Nature Jun. 8, 2000, vol. 405; 665-668.
You, L et al., "Directed evolution of *subtilis* in E in *Bacillus subtilis* to enhance total activity in aqueous dimethylformamide", Protein Engineering 1994, vol. 9, No. 1; 77-83.
U.S. Appl. No. 12/365,289, "Office Action" mailed Feb. 8, 2012.
Baliga, et al., "Genomic and genetic dissection of an archaeal regulon", PNAS, Feb. 27, 2001, vol. 98, No. 5; 2521-2525.
Bamann, Christian et al., "Spectral Characteristics of the Photocycle of Channelrhodopsin-2 and Its Implication for Channel Function", J. Mol. Biol., 2008, 375: 686-694.
Bard, et al., "Artificial Photosynthesis: Solar Splitting of Water to Hydrogen and Oxygen", Acc. Chem. Res, 1995, 28; 141-145.

(Continued)

*Primary Examiner* — Anand Desai
(74) *Attorney, Agent, or Firm* — Kilpatrick Townsend & Stockton LLP

(57) ABSTRACT

Bacteriorhodopsin protein variants and methods using the bacteriorhodopsin variants for performance in holographic and three-dimensional (3D) memory storage devices are described. The amino acid and chemical modifications of bacteriorhodopsin provided herein achieve greatly enhanced protein performance. The memory storage devices write, read and erase data proficiently. The bacteriorhodopsin protein variants are useful in optical memory storage and associative processor systems. Irradiation of the light-sensitive protein with light of known wavelength causes the protein to switch between different states. The variants enter the branched photocycle via a single or a two photon process and form the permanent 'Q' state more efficiently than the wild-type bacteriorhodopsin protein. This branching photocycle of the variants is exploited in the fabrication of 3D memory storage devices.

17 Claims, 12 Drawing Sheets
(11 of 12 Drawing Sheet(s) Filed in Color)

(56) References Cited

OTHER PUBLICATIONS

Berthold, Peter et al., "Channelrhodopsin-1 Initiates Phototaxis and Photophobic Responses in *Chlamydomonas* by Immediate Light-Induced Depolarization", The Plant Cell, 2008, vol. 20: 1665-1677.
Birnboim, , "A Rapid Alkaline Extraction Method for the Isolation of Plasmid DNA", Methods in Enzymology, 1983, vol. 100; 243-255.
Branden, et al., "Introduction to Protein Structure", Garland Publishing Inc., New York, 1991, 247.
Bringmann, Andreas et al., "Mammalian Retinal Glial (Muller) Cells Express Large-Conductance Ca2+-Activated K+ Channels That Are Modulated by Mg2+ and pH and Activated by Protein Kinase A", GLIA, 1997, 19:311-323.
Bromley, Keith M. et al., "Bio-Functional Mesolamellar Nanocomposites Based on Inorganic/Polymer Intercalation in Purple Membrane (Bacteriorhodopsin) Films", Advanced Materials, 2007, 19: 2433-2438.
Chen, Zhongping et al., "Bacteriorhodopsin oriented in polyvinyl alcohol films as an erasable optical storage medium", Applied Optics, 1991, vol. 30, No. 35, 5188-5196.
Chen, Zhongping et al., "Protein-based artificial retinas", TIBTECH, 1993, vol. 11: 292-300.
Cline, Steven W. et al., "Transformation methods for halophilic archaebacteria", Can. J. Microbiol., 1989, vol. 35, 148-152.
Crittenden, et al., "Soft lithography based micron-scale electrophoretic patterning of purple membrane", J. Micromech. Microeng., 2005, 15; 1494-1497.
Douglass, Adam D. et al., "Escape Behavior Elicited by Single, Channelrhodopsin-2-Evoked Spikes in Zebrafish Somatosensory Neurons", Current Biology, 2008, 18: 1133-1137.
Dyukova, et al., "Optical and electrical characterization of bacteriorhodopsin films", Biosystems, 1997, 41, pp. 91-98.
Enz, Ralf et al., "Expression of the Voltage-Gated Chloride Channel CIC-2 in Rod Bipolar Cells of the Rat Retina", The Journal of Neuroscience, 1999, 19(22):9841-9847.
Essen, Lars-Oliver, "Halorhodopsin: light-driven ion pumping made simple?", Current Opinion in Structural Biology, 2002, 12:516-522.
Ettaiche, Mohamed et al., "Acid-Sensing Ion Channel 2 is Important for Retinal Function and Protects against Light-Induced Retinal Degeneration", The Journal of Neuroscience, 2004, 24(5):1005-1012.
Georgescu, Radu et al., "Saturation Mutagenesis", Methods in Molecular Biology, 2003, vol. 231; 75-83.
Gillespie, Nathan B. et al., "Characterization of the Branched-Photocycle Intermediates P and Q of Bacteriorhodopsin", J. Phys. Chem, 2002, 106, 13352-13361.
He, et al., "Oriented Bacteriorhodopsin/Polycation Multilayers by Electrostatic Layer-by-Layer Assembly", Langmuir, 1998, 14; 1674-1679.
He, Jin-An et al., "Bacteriorhodopsin Thin Film Assemblies—Immobilization, Properties, and Applications", Advanced Materials, 1999, 11, No. 6: 435-446.
He, Jin-An et al., "Oriented Bacteriorhodopsin/Polycation Multilayers by Electrostatic Layer-by-Layer Assembly", Langmuir, vol. 14, No. 7, Feb. 13, 1998, 1674-1679.
He, Jin-An et al., "Photoelectric Properties of Oriented Bacteriorhodopsin/Polycation Multilayers by Electrostatic Layer-by-Layer Assembly", J. Phys. Chem., 1998, 102, 7067-7072.
Hillebrecht, et al., "Directed Evolution of Bacteriorhodopsin for Device Applications", Methods in Enzymology, 2004, vol. 388; 333-347.
Hillebrecht, Jason R., "The Characterization and Optimization of Photoactive Proteins for Performance in Optoelectronic Device Applications", A dissertation; Syracuse University, 2000, 1-179.
Hsu, et al., "Reversal of the surface charge asymmetry in purple membrane due to single amino acid substitutions.", Biophys J. 70(5), May 1996, 2358-2365.
Konnerth, A et al., "Proton-Induced Transformation of Calcium Channel in Chick Dorsal Root Ganglion Cells", J. Physiol., 1987, 386: 603-633.
Koyama, Koichi et al., "Antibody-Mediated Bacteriorhodopsin Orientation for Molecular Device Architectures", Science, 1994, 265: 762-765.
Liu, Yunxiao et al., "Layer-by-Layer assembly of biomacromolecules on poly(ethylene terephthalate) films and fiber fabrics to promote endothelial cell growth", J. Biomed. Mater. Res., 2007, 81A: 692-704.
Liu, Yunxiao et al., "Surface modification of poly(ethylene terephthalate) via hydrolysis and layer-by-layer of chitosan and chondroitin sulfate to construct cytocompatible layer for human endothelial cells", Colloids and Surfaces, 2005, 46: 117-126.
Marc, Robert E., "Kainate Activation of Horizontal, Bipolar, Amacrine, and Ganglion Cells in the Rabbit Retina", The Journal of Comparataive Neurology, 1999, 407:65-76.
Nagel, Georg et al., "Channelrhodopsin-1: A Light-Gated Proton Channel in Green Algae", Science, 2002, vol. 296: 2395-2398.
Nagel, Georg et al., "Channelrhodopsin-2, a directly light-gated cation-selective membrane channel", PNAS, 2003, 100(24): 13940-13945.
Paula, Stefan et al., "Roles of Cytoplasmic Arginine and Threonine in Chloride Transport by the Bacteriorhodopsin Mutant D85T", Biophysical Journal, 2001, vol. 80: 2386-2395.
PCT/US2010/026362, , "International Search Report", Dec. 22, 2010.
PCT/US2010/026362, International Preliminary Report on Patentability and Written Opinion, Published Feb. 3, 2011.
Peralvarez, et al., "Thr90 i s a key residue of the bacteriorhodopsin proton pumping mechanism", FEBS Letters, Elsevier, Amsterdam, NLLNKD-DOI:10.1016/50014-5793(01)03080-0, Nov. 23, 2001, vol. 508, No. 3, 399-402.
Petreanu, Leopoldo et al., "Channelrhodopsin-2-assisted circuit mapping of long-range callosal projections", Nature Neuroscience, 2007, vol. 10(5):663-668.
Pfeiffer, et al., "Site-directed spin-labeling reveals the orientation of the amino acid side-chains in the E-F loop of bacteriorhodopsin", J Mol Biol., vol. 287, Issue 1, Mar. 19, 1999, 163-171.
Phaneuf, Matthew D. et al., "Modification of Polyethylene Terephthalate (Dacron) Via Denier Reduction: Effects on Material Tensile Strength, Weight, and Protein Binding Capabilities", Journal of Applied Biomaterials, 1995, vol. 6:289-299.
Ranaghan, et al., "Photochemical and thermal stability of green and blue proteorhodopsins: implications for protein-based bioelectronic devices", J Phys Chem B. vol. 114(44), 14064-70, (2010).
Sasaki, Jun et al., "Conversion of Bacteriorhodopsin into a Chloride Ion Pump", Science, 1995, vol. 269: 73-75.
Sasaki, Jun et al., "Conversion of Bacteriorhodopsin into a Chloride Ion Pump", Science, 7/7/19, vol. 269; 73.
Schranz, et al., "Oriented Purple Membrane Monolayers Covalently Attached to Gold by Multiple Thiole Linkages Analyzed by Single Molecule Force Spectroscopy", Langmuir, 2007, 23; 11134-11138.
Theogarajan, Luke S., "Supramolecular Architectures for Neural Prostheses", Doctoral Thesis—Massachusetts Institute of Technology, 2007, 1-230.
Varo, G et al., "Photoelectric Signals from Dried Oriented Purple Membranes of *Halobacterium halobium*", Biophys. J., 1983, vol. 43: 47-51.
Verweij, J et al., "Horizontal Cells Feed Back to Cones by Shifting the Cone Calcium-Current Activation Range", Vision Res., 1996, vol. 36, No. 24:3943-3953.
Wise, et al., "Optimization of bacteriorhodopsin for bioelectronic devices", Trends in Biotechnology, Sep. 2002, vol. 20, No. 9; 387-394.
Wyers, Marc C. et al., "In Vivo Assessment of a Novel Dacron Surface with Covalently Bound Recombinant Hirudin", Cardiovascular Pathology, 1999, vol. 8, No. 3:153-159.
Zhang, Yu-He et al., "Real-time Holographic imaging with a bacteriorhodopsin film", Optics Letters, 1995, vol. 20, No. 23:2429-2431.
Zrenner, Eberhart, "The Subretinal Implant: Can Microphotodiode Arrays Replace Degenerated Retinal Photoreceptors to Restore Vision?", Ophthalmologica, 2002, 216(suppl 1):8-20.
U.S. Appl. No. 12/365,289, "Office Action", Aug. 9, 2012.

(56) References Cited

OTHER PUBLICATIONS

Sanz et al., "Opening the Schiff base moiety of bacteriorhodopsin by mutation of the four extracellular Glu side chains.", FEBS Lett,, Jul. 30, 1999, 191-5.
Amendment to Apr. 27, 2012 Final Office Action dated Jul. 27, 2012 in related U.S. Appl. No. 12/353,282.
Amendment to Aug. 16, 2011 Nonfinal Office Action dated Feb. 16, 2012 in related U.S. Appl. No. 12/353,282.
U.S. Appl. No. 12/365,289, "Advisory Action" dated Oct. 17, 2012, 3 pages.
U.S. Appl. No. 12/718,780, "Notice of Allowance" dated Jun. 14, 2013, 12 pages.
U.S. Appl. No. 12/718,780, "Office Action" dated Nov. 7, 2012, 20 pages.
Alexiev et al., "Rapid long-range proton diffusion along the surface of the purple membrane and delayed proton transfer into the bulk", Proc. Natl. Acad. Sci. USA, 92, 1995, 372-376.
Alexiev et al., "Evidence for Long Range Allosteric Interactions between the Extracellular and Cytoplasmic Parts of Bacteriorhodopsin from the Mutant R82A and Its Second Site Revertant R82A/G231C", Journal of Biological Chemistry, vol. 275, No. 18, May 5, 2000, pp. 13431-13440.
Alexiev et al., "Surface Charge of Bacteriorhodopsin Detected with Covalently Bound pH Indicators at Selected Extracellular and Cytoplasmic Sites", Biochemistry, 33, 1994, 298-306.
Dale et al., "Membrane Insertion Kinetics of a Protein Domain in Vivo—The Bacterioopsin N Terminus Inserts Co-Translationally", The Journal of Biological Chemistry, 274(32), 1999, 22693-8.
Dale et al., "Ordered membrane insertion of an archaeal opsin in vivo", PNAS, 97(14), 2000, 7847-7852.
Dunn et al., "The bacteriorhodopsin gene", Proc. Natl. Acad. Sci. USA, 78 (11), 1981, 6744-6748.
Eliash et al., "Specific Binding Sites for Cations in Bacteriorhodopsin", Biophysical Journal, 81, 2001, 1155-1162.
Hauser et al., "Interpretation of Amide I Difference Bands Observed during Protein Reactions Using Site-Directed Isotopically Labeled Bacteriorhodopsin as a Model System", J. Phys. Chem. A, 106, 2002, 3553-3559.
Heyne et al., "Reaction Control in Bacteriorhodopsin: Impact of Arg82 and Asp85 on the Fast Retinal Isomerization, Studied in the Second Site Revertant Arg82A1a/Gly231Cys and Various Purple and Blue Forms of Bacteriorhodopsin", J. Phys. Chem. B, 104, 2000, 6053-6058.
Lazarova et al., "Fourier Transform Infrared Evidence for Early Deprotonation of Asp85 at Alkaline pH in the Photocycle of Bacteriorhodopsin Mutants Containing E194Q", Biophysical Journal, 78, 2000, 2022-2030.
Martinez et al., "Subdomains in the F and G Helices of Bacteriorhodopsin Regulate the Conformational Transitions of the Reprotonation Mechanism", Proteins: Structure, Function, and Genetics, 48, 2002, 269-282.
Petkova et al., "Arginine Activity in the Proton-Motive Photocyle of Bacteriorhodopsin: Solid-State NMR Studies of the Wild-Type and D85N Proteins", Biochemistry, 38, 1999, 1562-1572.
Pfeiffer, "Studies on dynamics and function of Bacteriorhodopsin from *Halobacterium salinarum*", 2000.
Rink et al., "Spin-Labeling Studies of the Conformational Changes in the Vicinity of D36, D38, T46 and E161 of Bacteriorhodopsin during the Photocycle", Biophysical Journal, 73, 1997, 983-993.
Schatzler et al., "Subsecond Proton-Hole Propagation in Bacteriorhodopsin", Biophysical Journal, 84, 2003, 671-686.
Steinhoff et al., "Azide Reduces the Hydrophobic Barrier of the Bacteriorhodopsin Proton Channel", Biophysical Journal, 76, 1999, 2702-2710.
Varo et al., "Binding of Calcium Ions to Bacteriorhodopsin", Biophysical Journal, 76, 1999, 3219-3226.
Yamaguchi et al., "Surface Dynamics of Bacteriorhodopsin as Revealed by 13C NMR Studies on [13C] Ala-Labeled Proteins: Detection of Millisecond or Microsecond Motions in Interhelical Loops and C-Terminal a-Helix", J. Biochem, 129, 2001, 373-382.
Zimanyi et al., "Pathway of Proton Uptake in the Bacteriorhodopsin Photocycle", Biochemistry, 32, 1993, 7669-7678.
U.S. Appl. No. 12/365,289, "Non-Final Office Action", Aug. 14, 2014, 21 pages.

\* cited by examiner

US 8,883,719 B2

BACTERIORHODOPSIN PROTEIN VARIANTS AND METHODS OF USE FOR LONG TERM DATA STORAGE

This invention was made with government support under HR0011-05-1-0027 awarded by the Federal Defense Advanced Research Projects Agency and CCF-0432151 awarded by the National Science Foundation. The government has certain rights in the invention.

BACKGROUND OF THE INVENTION

Present day opto-electronic devices are constructed from materials that are capable of switching between two states, bit 0 and bit 1, either by the generation of electrons or magnetic fields. Recent advancements in optical technology resulted in the invention of compact-disk read-only memories (CD-ROM's) and magneto-optical read write memories (CDRW). The contemporary data storage media utilizes a two-dimensional design restricting them to serial data processing with a storage density of 12.5 million bytes per square centimeter. Numerous attempts have been made to formulate a three-dimensional memory device without success.

For example, U.S. Pat. No. 5,268,862 describes the use of an active photochromic material, spirobenzopyran in a polymeric matrix for use in 3D memory. The process of writing is a two photon process and requires the heterolytic cleavage of spirobenzopyran into a stable merocyanine complex. Reading of the data is initiated by the exposure of merocyanine to light, which causes fluorescence. Unfortunately, the photochemistry in this proposed 3D memory is not confined to a specific region, resulting in unwanted photochemical reactions in the adjacent cells outside the exposed area.

U.S. Pat. No. 5,253,198 describes the use of field-oriented bacteriorhodopsin in a polymer matrix. Orthogonally placed laser beams converge on the bacteriorhodopsin matrix to record a bit cell. A cleaning process is carried by actuating the two lasers non-simultaneously. The bit is read by actuating the lasers and reading the difference between bit 0 and bit 1 from the electric signal generated. One of the disadvantages to this matrix lies in the necessity to mechanically orient the memory cube relative to the lasers. This inadvertently causes unwanted side reactions in the adjacent bit cells.

U.S. Pat. No. 5,559,732 describes the branched photocycle memory architecture of bacteriorhodopsin for optical memories. The write process is a two-photon process, which involves a sequential one-photon route. U.S. Pat. Application Publication No 20060187795 A1 describes the creation of a 3D memory with the formation of a non-volatile state that is used in the read/write process.

Present day computational algorithms are limited in part by the lack of an efficient data storage media. To date, silicon-based memory chips are limited in their storage capacity and any improvements in this feature will become increasingly expensive. The persistent marketable force for smaller, faster and cheaper device components is pushing the existing technologies to their limits. This imposes the need for alternative technologies with economical storage/cost ratio to satisfy the proliferating demand for high throughput storage devices.

Bacteriorhodopsin-based protein optical memories offer great potential. These memories can be configured for thin-film photochromic, 3D branched-photocycle, holographic-binary or Fourier-transform holographic associative storage. The storage medium is lightweight, radiation hardened and relatively inexpensive, and combined with the inherent quantum efficiency and cyclicity of the protein, provides comparative advantages over present day organic and inorganic media. Nevertheless, the native protein is not optimal for any of the above-mentioned optical memories.

Therefore, what is needed is an alternative technology to silicon-based memory chips for the production of an inexpensive three-dimensional memory device having high throughput storage without adverse side reactions in adjacent bit cells.

BRIEF SUMMARY OF THE INVENTION

Bacteriorhodopsin variants and methods using the bacteriorhodopsin variants for performance in holographic and three-dimensional (3D) memory storage devices are provided. Using the 3D architecture provides storage density improvements relative to two dimensional designs (which are limited by the necessary serial processing). While nature has optimized the native protein extensively for performance in devices, the genetic and chemical modifications of bacteriorhodopsin described herein provide greatly enhanced protein performance. The genetically modified bacteriorhodopsin-based memory devices described herein write, read and erase data proficiently. A feature is in the use of the photochromic substance of bacteriorhodopsin and variants thereof (such as V49X, T90X, D115X, E204X, E194X, L206X, D85X/D96X, T90X/V49X/E204X) in optical memory storage and associative processor systems. Irradiation of the light-sensitive protein with light of known wavelength causes the protein to switch between different states. The genetically engineered bacteriorhodopsin variants enter the branched photocycle via a single photon or a two photon process to form the permanent 'Q' state more efficiently relative to that of wild-type protein. This branching photocycle of the variants is exploited in the fabrication of 3D memory storage devices. The memory functions by assigning the main photocycle as bit 0 and the branched photocycle (P and Q states, respectively) as bit 1. The protein-based memory architecture has implications in the generation of ultra-high density RAMs. The protein-based devices offer a comparative advantage over modern-day semiconductors based on the scale, speed and efficiency with which these molecules process information. The unique architecture, size, cyclicity, and natural resistance to harsh environmental conditions gives protein-based memories a relative advantage over magnetic and optical data storage devices.

BRIEF DESCRIPTION OF THE SEVERAL VIEWS OF THE DRAWING

The patent or application file contains at least one drawing executed in color. Copies of this patent or patent application publication with color drawing(s) will be provided by the Office upon request and payment of the necessary fee.

DETAILED DESCRIPTION

Bacteriorhodopsin variants and methods using the variants for performance in holographic and three-dimensional (3D) memory storage devices are described. The genetic and chemical modifications of bacteriorhodopsin described herein provide greatly enhanced protein performance. The genetically modified bacteriorhodopsin-based memory devices provided herein write, read and erase data proficiently.

Figure 4:
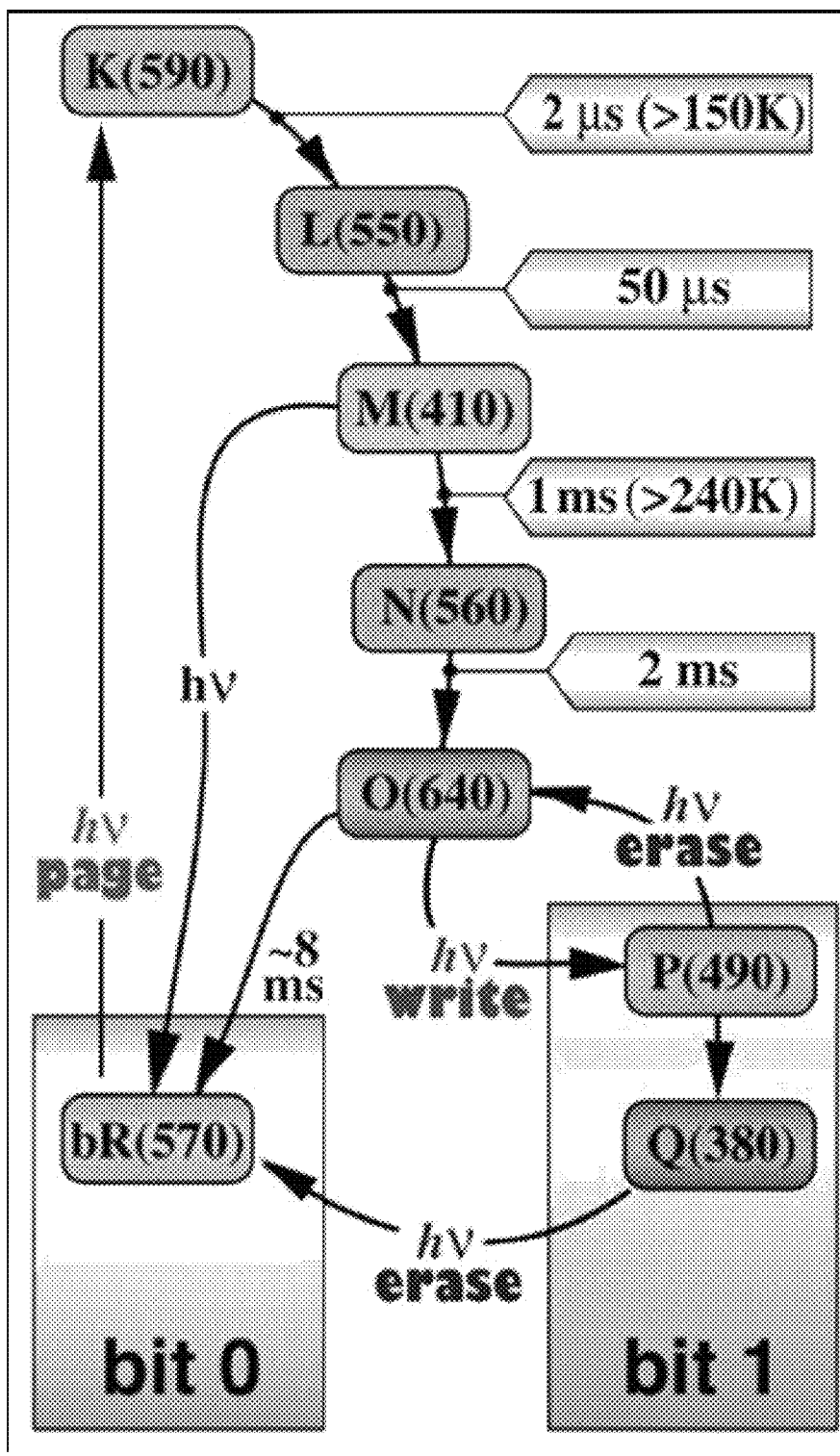
FIG. 4 shows the photocycle of bacteriorhodopsin.

Bacteriorhodopsin is a membrane-bound light-transducing protein that functions as a proton pump in the archaeon *Halobacterium salinarum* (previously known as *Halobacterium halobium* or *Halobacterium salinarium*). *H. salinarum* has adapted to high salt environments (5 M or 25% NaCl) and can use bacteriorhodopsin to absorb light energy and convert it to chemical energy. In response to low oxygen availability, *H. salinarum* produces a purple membrane, in which thousands of bacteriorhodopsin trimers are assembled in a 2D hexagonal lattice. Although bacteriorhodopsin is crucial for long-term cellular survival when oxygen is limited, the protein is not essential under aerobic conditions, because *H. salinarum* can also obtain energy from respiration. Each bacteriorhodopsin molecule consists of two components: a 248 amino acid polypeptide (bacterio-opsin or BO) and a chemical chromophore (retinal) embedded in the middle of the protein. The proton pumping process of bacteriorhodopsin is initiated when the chromophore absorbs light and undergoes a photocycle as schematically shown in FIG. 4. Although many aspects of the proton-pumping mechanism remain to be discovered, much has been learned about the molecular details during the past few years.

One embodiment described herein is the use of the photochromic substance of bacteriorhodopsin and its variants in optical memory storage and associative processor systems. The irradiation of the light-sensitive protein with light of known wavelength causes the protein to switch between different states. In one variation, the genetically engineered bacteriorhodopsin variants enter the branched photocycle via a single photon process and form the permanent 'Q' state efficiently relative to that of wild-type protein (see FIG. 4). In this embodiment, the branching photocycle of the variants are exploited in the fabrication of 3D memory storage devices. In one variation, the memory functions by assigning the main photocycle as bit 0 and the branched photocycle (P and Q states, respectively) as bit 1. In this variation, the protein-based memory architecture can be used in the generation of ultra-high density RAMs. Irradiation of the Q state with a wavelength of a different frequency can be used to achieve a different state and can be used to erase the written data. In one embodiment, the genetically engineered bacteriorhodopsin variants enter the branched photocycle via a two photon process to form the permanent Q state. See, for example, FIG. 4 wherein the Q state can be transformed to a different state represented by bR. It should be recognized that the P state can also be irradiated with a wavelength of a given different frequency to achieve the O state. This also has the effect of erasing written data.

The protein-based devices described herein offer a comparative advantage over modern-day semiconductors based on the scale, speed and efficiency with which these molecules process information. The unique architecture, size, cyclicity, and natural resistance to harsh environmental conditions give protein-based memories a relative advantage over magnetic and optical data storage devices.

The bacteriorhodopsin variants and methods of use are described in further detail with reference to the figures below. It should be understood that the figures are merely illustrative embodiments of the present invention and should not be construed to limit the present invention, but are merely provided for an understanding of the invention.

Figure 1:
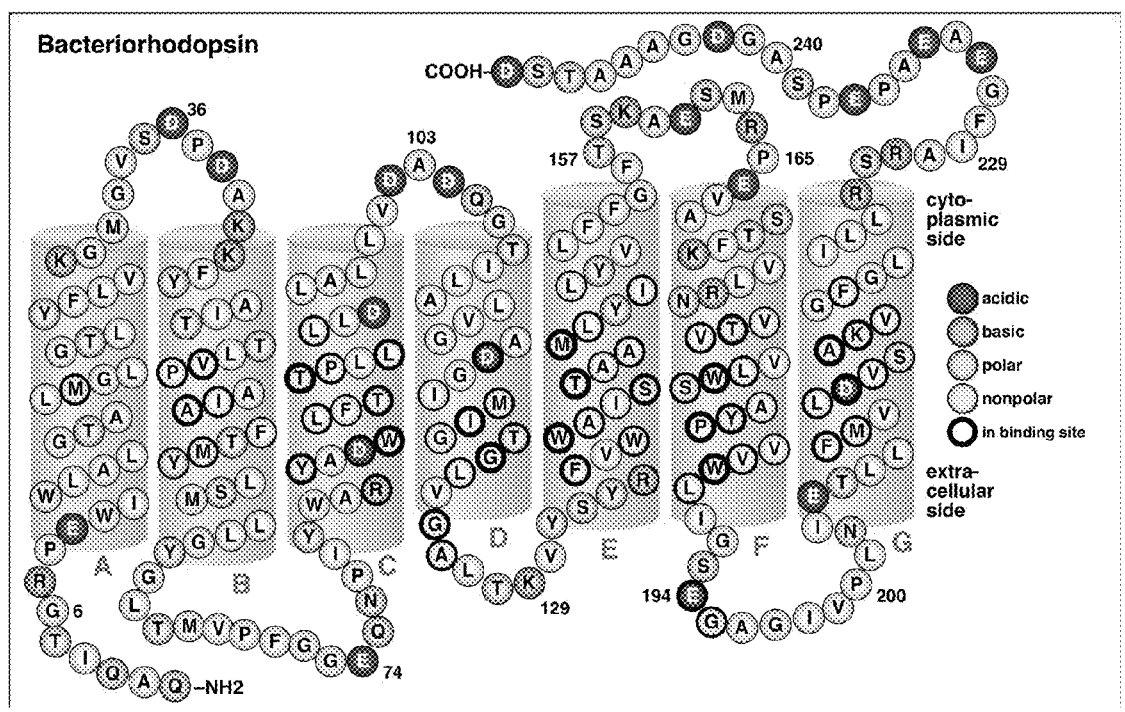
FIG. 1 shows a secondary structure model of bacteriorhodopsin.

FIG. 1 shows a secondary structure model of bacteriorhodopsin (BR). A snake plot representation of the seven transmembrane α-helical domains with three alternating loop regions is shown. Residues projected to constitute the retinal-binding pocket in BR are circled and appear in the interior of the protein. Residues constituting the protein are colored based on their properties with acidic residues shown in black; basic residues are red; polar amino acids are green and non-polar residues are gray. Bacteriorhodopsin variants with enhanced photochromic properties have primarily resulted from mutations to the wild-type protein that have been engineered in the retinal-binding pocket (for example, to V49, T90, D115, D85) of the protein.

Figure 2:
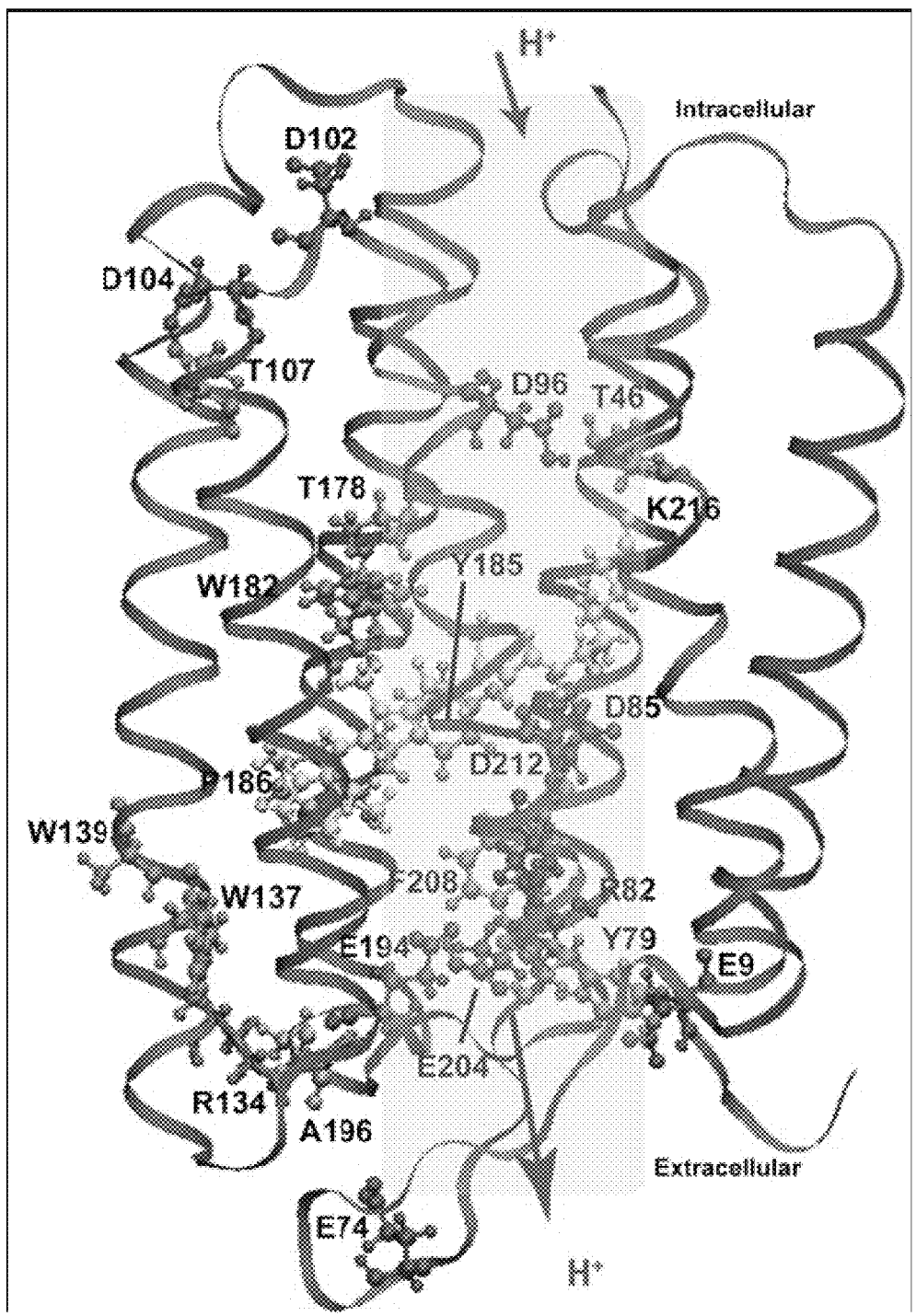
FIG. 2 shows a 3D model of bacteriorhodopsin based on 1C3W crystal structure (1.55 Å).

FIG. 2 shows a 3D ribbon model of BR based on 1C3W crystal structure (1.55 Å). The protein is characterized by the presence of seven transmembrane regions with an all-trans retinal bound via K216 (shown in orange). The seven transmembrane regions can also be seen in FIG. 1. Highlighted in FIG. 2 are several of the key residues in the protein (V49, T46, R82, D85, L93, D96, E194, E204 and D212).

Figure 3:
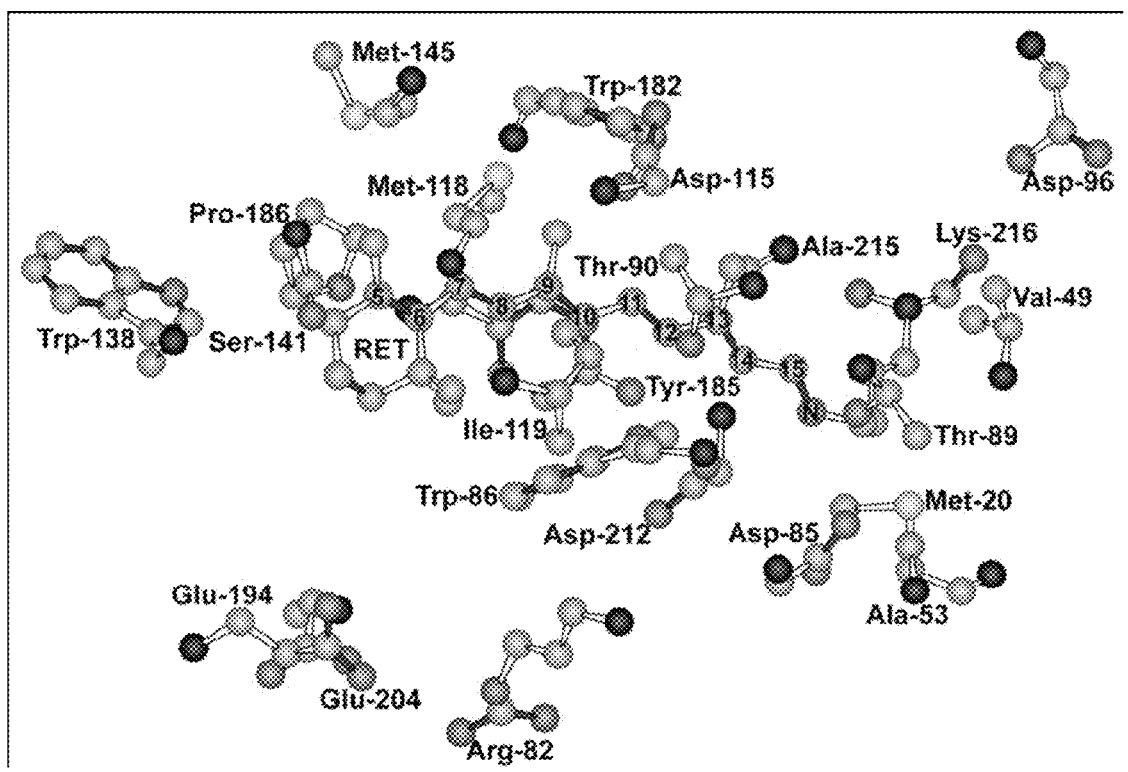
FIG. 3 shows a retinal-binding pocket of bacteriorhodopsin based on the 1C3W (1.55 Å) crystal structure.

FIG. 3 shows a ball and stick depiction of the retinal-binding pocket of BR based on the 1C3W(1.55 Å) crystal structure (as seen in FIG. 2). Shown in FIG. 3 are several residues lining the binding pocket extracted at a distance of up to 3.6 Å from the chromophore, retinal with several key residues Val-49, Asp-85, Thr-90, Asp-96, Asp-115, Glu-194 and Lys-216 highlighted.

FIG. 4 shows a schematic depiction of the photocycle of bacteriorhodopsin. When BR absorbs light, the protein undergoes conformational changes that are relayed as spectrally discrete photointermediate states constituting a photocycle. The absorption maximum of the M state in the BR main photocycle is considerably blue-shifted while that of the O state is red-shifted relative to the resting state, bR in the native protein. Paging the O state with red light leads into the branched photocycle, characterized by the P and Q state (which is how writing to the data storage device is achieved). Formation of the Q state in wild-type bacteriorhodopsin is via a sequential one-photon process (resulting in a two-photon process).

Figure 5:
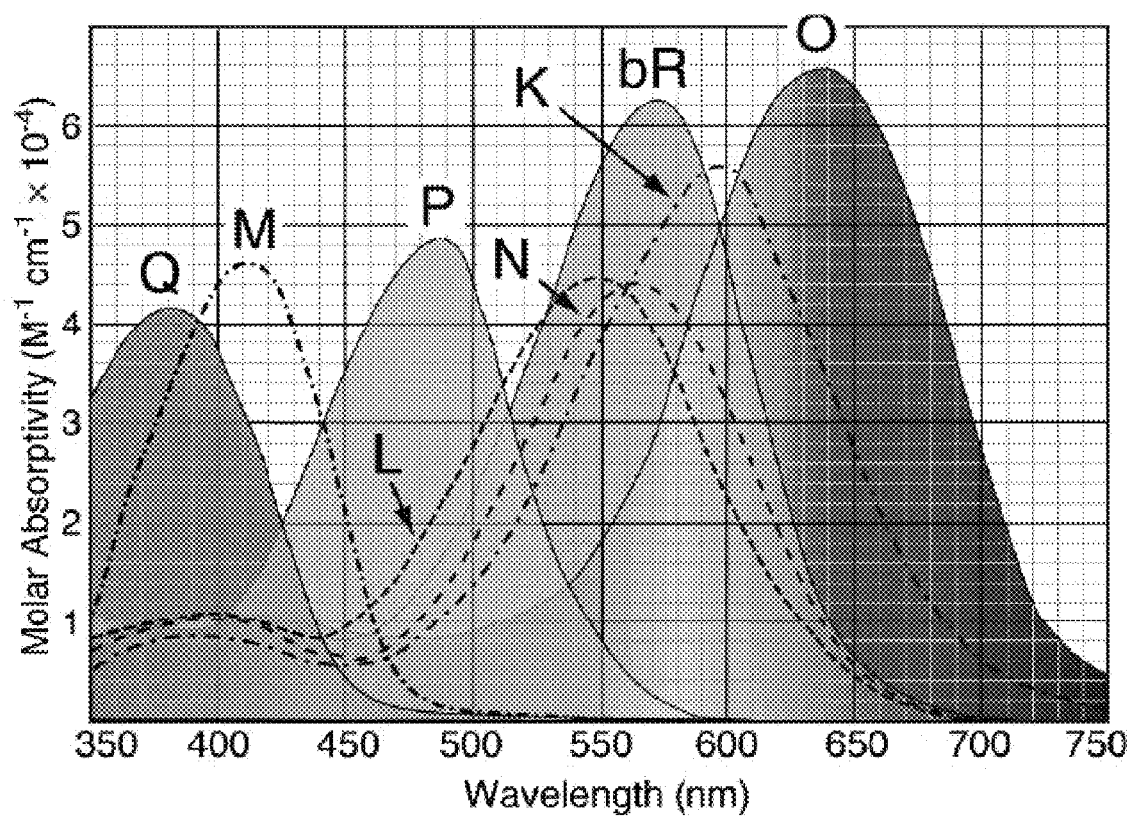
FIG. 5 shows the absorption maxima of the photointermediates that constitute the bacteriorhodopsin photocycle under ambient room temperature conditions.

FIG. 5 shows the absorption maxima of the photointermediates that constitute the BR photocycle under ambient room temperature conditions. It should be noted that the absorption maxima are sufficiently discrete from each other so that one can selectively achieve the various states of the bacteriorhodopsin.

Figure 6:
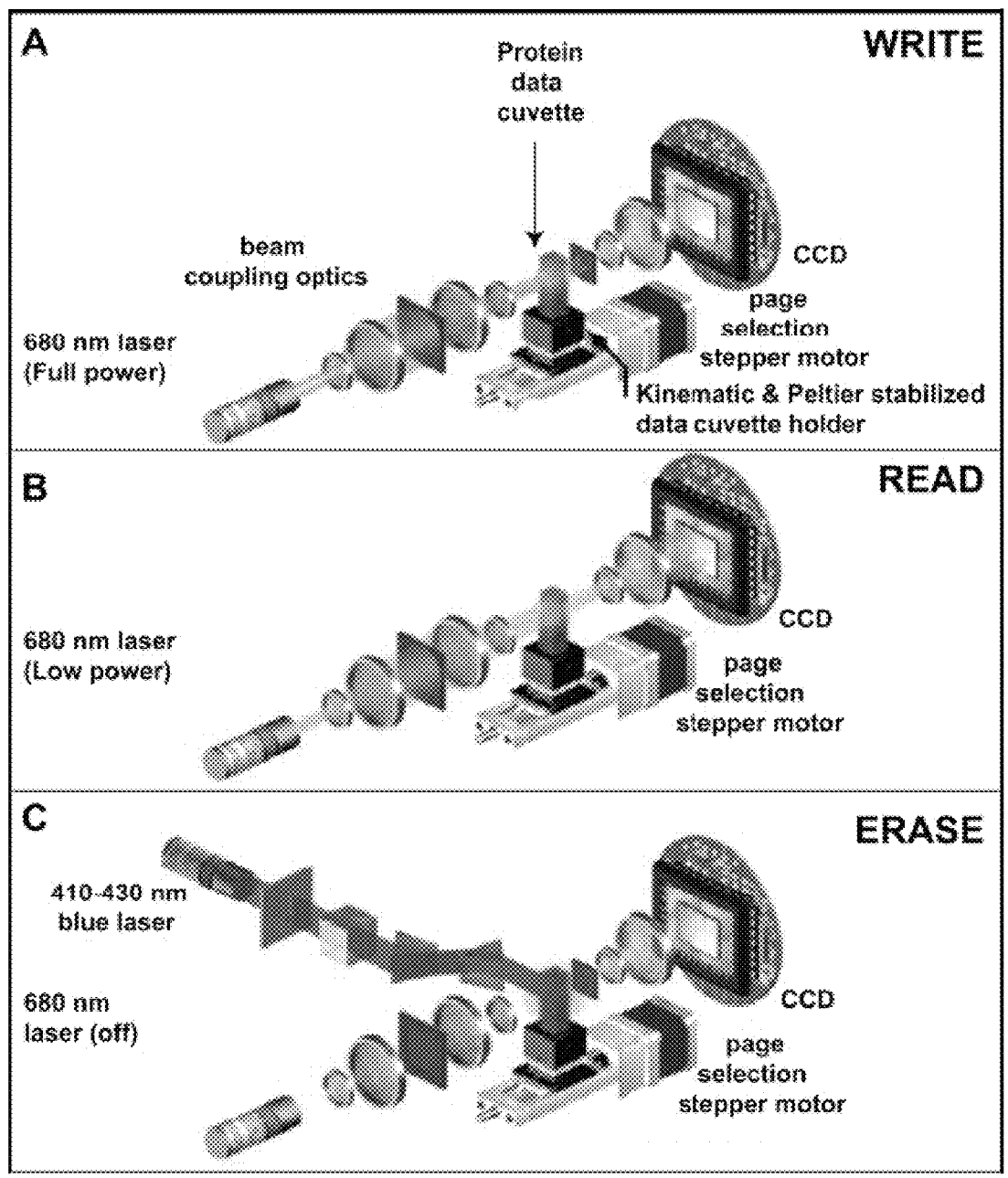
FIG. 6 shows the write (A), read (B) and erase (C) operations of the bacteriorhodopsin variant-based branched-photocycle memory as a single photon process

FIG. 6 shows a depiction of how the write (A), read (B) and erase (C) operations of the bacteriorhodopsin variant-based branched-photocycle memory occur via a single photon process. The write and read operations are both initiated by using a paging beam to activate the photocycle in a thin region within the memory medium (using red light at different intensities). That is, the read process is similar to the write process, but in the read process a low powered paging beam is turned on so that just enough light gets through to image the page onto the CCD (or CID) array. A blue laser erases an entire page (as shown in FIG. 6C). The three dimensional nature should be apparent from FIG. 6C.

Figure 7:
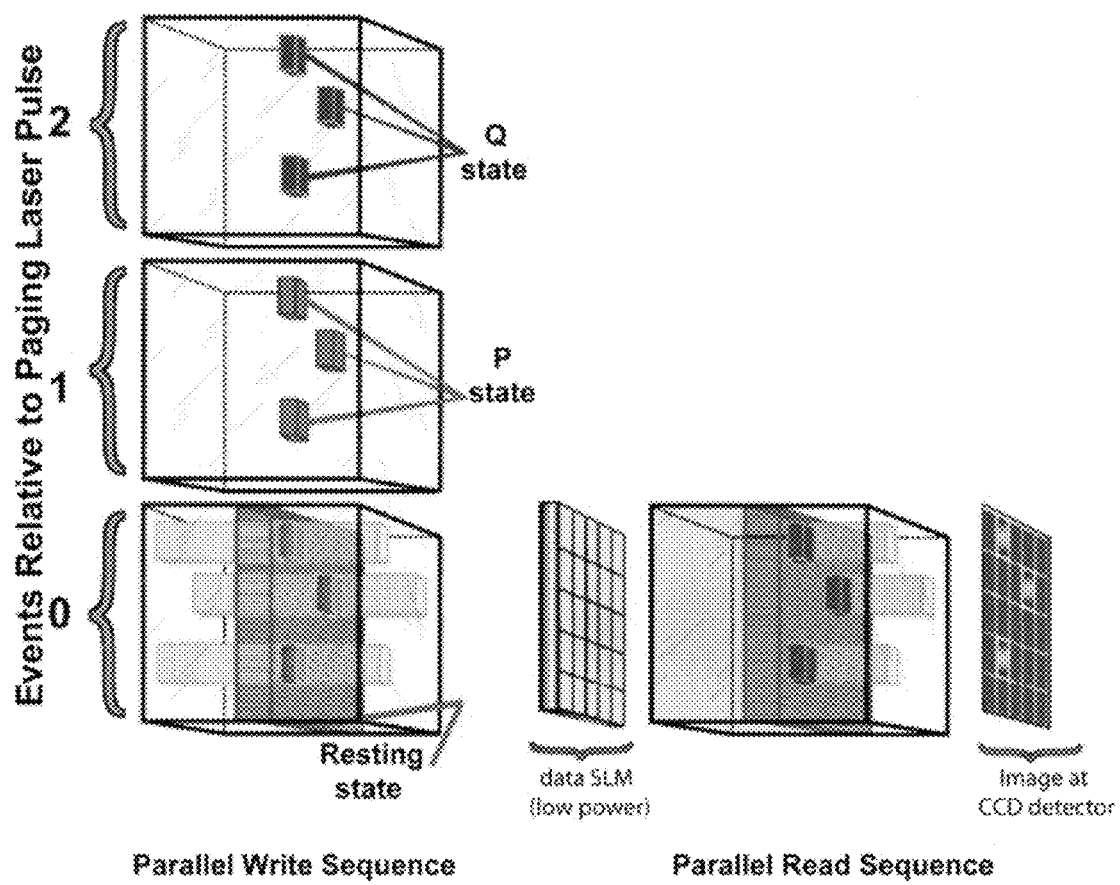
FIG. 7 shows a parallel write (left) and read processes (right) using the protein-based 3D memory of a bacteriorhodopsin variant in a single photon process

FIG. 7 shows parallel write (left) and read (right) processes using the proposed protein-based 3D memory (single photon process). Paging specific volumes within the cuvette containing the BR-variant with red light converts the resting state into a P state that thermally relaxes to the permanent Q state. This process is associated with the act of writing data onto the volumetric cube (and is shown in the Figure by 0, 1, and 2 for the events relative to the paging laser pulse). Irradiation of the cuvette with a low-powered red light images the activated page on the CCD detector, which generally possesses the capability of the detector to distinguishing the paged region versus the unpaged region. The data written on the volumetric cube can be erased by exposure to blue light. The high energy associated with blue light causes the conversion of the 9-cis chromophore into an all-trans configuration resulting in the formation of the resting state (bit 0).

Figure 8:
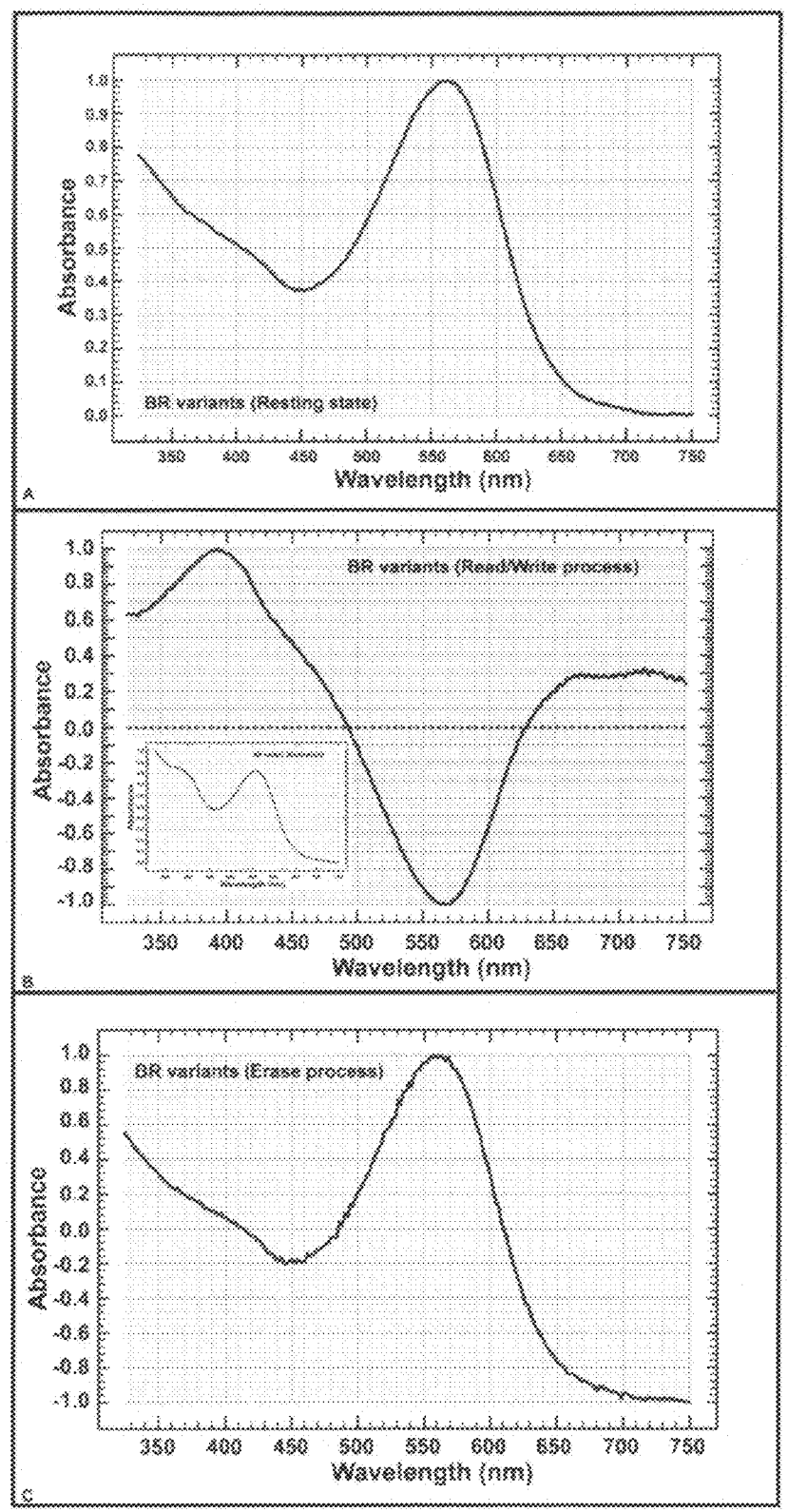
FIG. 8 shows efficient Q formation in bacteriorhodopsin variants.

FIG. 8 shows efficient Q formation in bacteriorhodopsin variants. Illumination of the resting state of BR variants (as shown in Panel A) with red light drives the protein to form the permanent Q state (as shown in Panel B—note the shift in the absorption maximum to a 390 nm peak), which is a component of the branched photocycle via a single photon process. The main and alternate photocycle in these bacteriorhodopsin variants can be envisioned as bit '0' (Panel A) and bit '1' (Panel B), respectively. Formation of the Q state in the bacteriorhodopsin variants can be associated with the write process. Differential illumination of the Q state converted regions in the bacteriorhodopsin containing cuvette facilitates the read process (for example, by a low powered pulse). Exposure of the cuvette to blue light results in the erasure of the Q state to reform the resting state and is associated with the erase process of the 3D memory architecture. Note the similarities between Panel A and Panel C.

Figure 9:
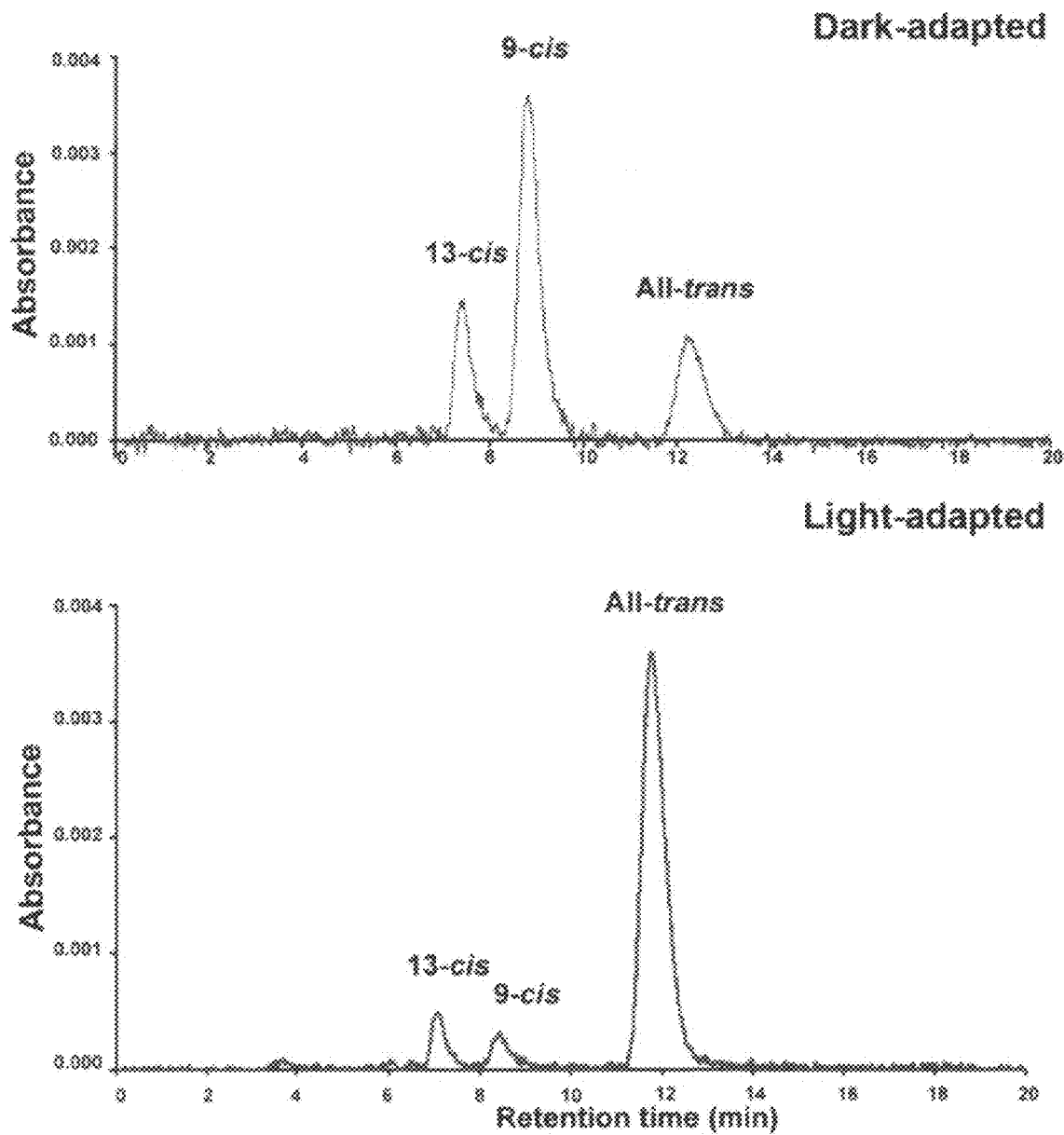
FIG. 9 shows retinal isomer ratios in the dark and light-adapted state of bacteriorhodopsin variant.

FIG. 9 shows a depiction of HPLC chromatograms with the retinal isomer ratios in the dark—(FIG. 9A) and light—(FIG. 9B) adapted state of the bacteriorhodopsin variant. The chromophore of dark-adapted and light-adapted bacteriorhodopsin variants were extracted with ethanol and analyzed using HPLC. Note that the dark-adapted state of the bacteriorhodopsin variants exhibits a higher contribution from the 9-cis isomer compared to the light-adapted state.

Figure 10:
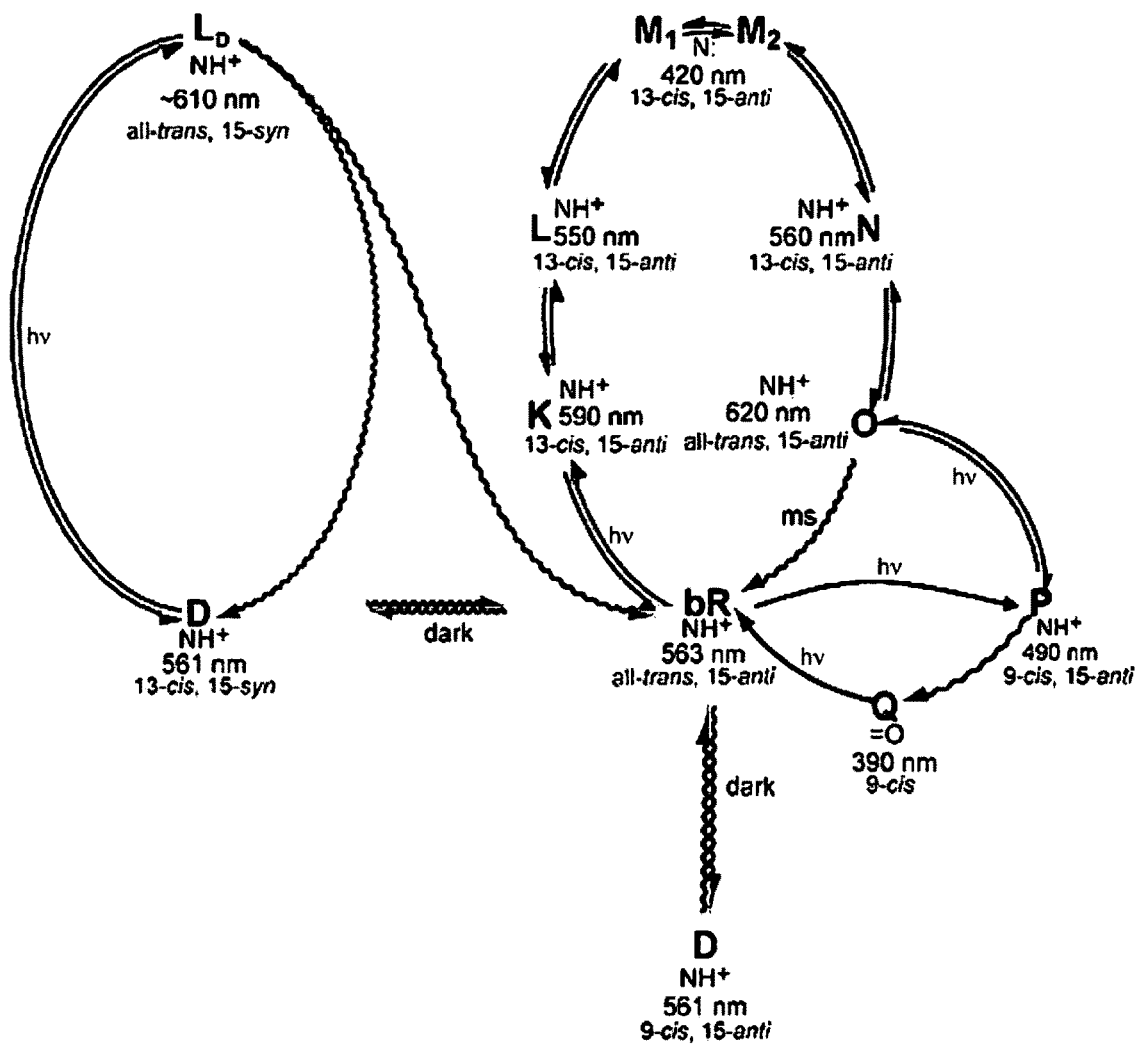
FIG. 10 shows proposed photocycle for genetically optimized bacteriorhodopsin variants.

FIG. 10 shows a proposed photocycle for genetically optimized bacteriorhodopsin variants. The all-trans, 15-anti retinal isomer in the light-adapted resting state of these bacteriorhodopsin variants form the permanent Q state via a single photon process as shown in this figure. In the dark-adapted state, there is an equilibrium between the 9-cis, 13-cis ($D^9$ and $D^{13}$) and the all-trans isomers.

Figure 11:
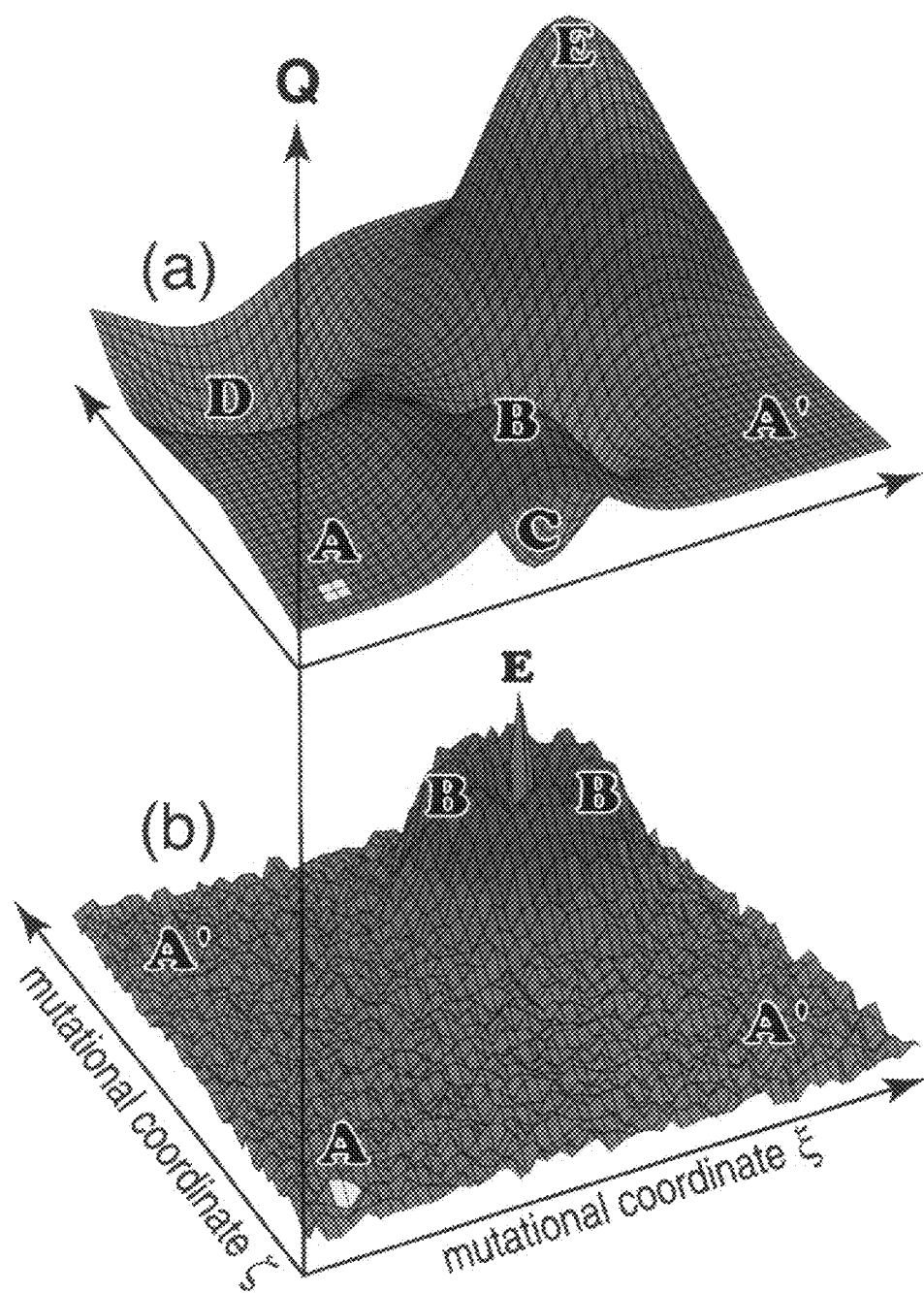
FIG. 11 shows hypothetical mutational landscapes for fluid traits (a) and spectrokinetic optimizations (b).

FIG. 11 shows a hypothetical mutational landscapes for fluid traits (a) and spectrokinetic optimizations (b). The native protein is located at the central locus of the yellow squares, the mutational coordinates $\xi$ and $\zeta$ are arbitrary, and the vertical axis measures an arbitrary Q factor. Starting at 'A', the ultimate goal of the mutational strategies described herein is to discover the optimal protein, represented by peak 'E' (wherein Q represents some factor that makes the protein ideally suited for writing and/or reading and/or erasing data more proficiently than the native protein). E represents a maximum peak of this value Q, which may be either a local maximum or a global maximum. The 'A' and 'A'' regions represent mutations that have little impact on the Q factor, the 'B' region may represent another local maxima in Q but a more optimal mutation in the landscape surveyed is at the peak labeled 'E'. Cyclical optimization will typically find 'E' in the fluid case, but is unlikely to find 'E' in the spectrokinetic optimization without good modeling or operator intuition. For fluid characters such as temperature, less variation is expected (see FIG. 11a wherein the mutational landscape tends to be smoother). The overall temperature stability of the protein might decrease (troughs 'C' or 'D'), but also has a comparable chance of increasing (peaks 'B' and 'E'). FIG. 11b shows the mutational landscape for more complex characteristics such as spectrokinetic properties, in which most of the performance is localized in specific regions of the protein (note the rough nature of the mutational landscape wherein small movement along either the $\xi$ or $\zeta$ axis may result in a positive or negative Q. In this landscape (11b), the mutational surface is probably a rugged landscape with numerous local minima (and also local maxima).

Figure 12:
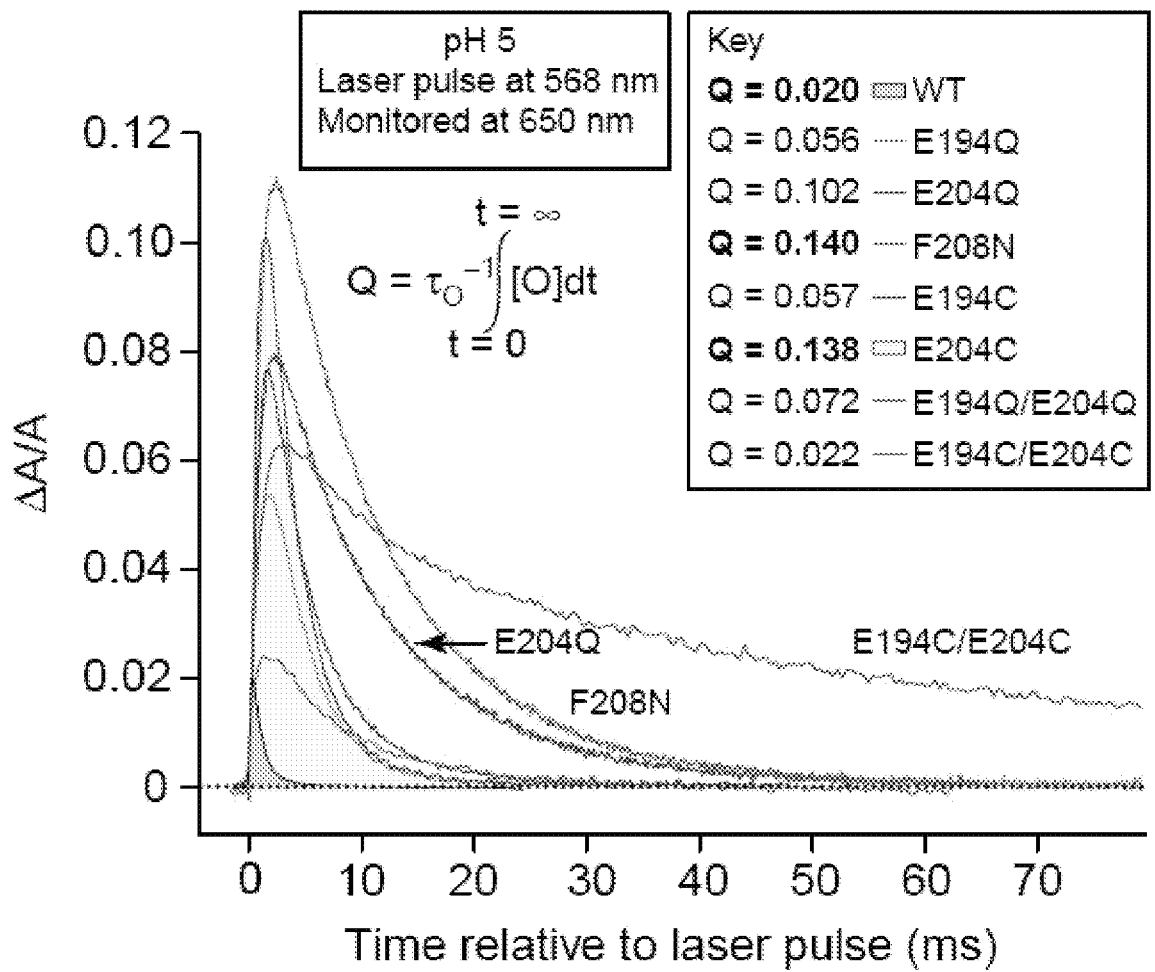
FIG. 12 shows the effect of mutations involving Glu194 and Glu204 on O state kinetics, measured at pH 5.0.

FIG. 12 shows the effect of mutations involving Glu194 and Glu204 on O state kinetics, measured at pH 5.0. Wild-type (WT) protein is shaded in green and has the smallest Q value of all the proteins studied. The O state lifetime in WT is 6-8 ms. The O state lifetimes of E194Q and E204Q are 70 ms and 125 ms, respectively. The double mutant E194C/E204C has the longest O state lifetime, with a lifetime of ~1 second. This represents more than a 100-fold increase in the O state decay time. Although the E194C/E204C double mutant has the longest O state lifetime, the E204Q mutant has the largest Q value (see FIG. 11, for example).

Accordingly, in an embodiment, bacteriorhodopsin variants for use in holographic and three-dimensional (3D) memory storage devices are provided. A feature described herein is a method of using or making the photochromic substance of bacteriorhodopsin and its variants (such as for example, V49X, T90X, D115X, E204X, E194X, L206X, D85X/D96X, V49X/T90X/E204X, the meaning of "X" is explained in more detail below, but generally signifies that X can be any amino acid that is not the same as the amino acid being replaced) in optical memory storage and associative processor systems. Irradiation of the light-sensitive protein with various lasers of different known wavelengths causes the protein to switch between different states. These different states include the native state and a branched photocycle state.

Accordingly, in one embodiment, the genetically engineered BR variants, after irradiation with a laser of given wavelength, enter the branched photocycle state via a single photon or a two photon process and form the permanent 'Q' state efficiently. This branching photocycle of the variants is exploited in the fabrication of 3D memory storage devices. The memory functions by assigning the main photocycle as bit 0 and the branched photocycle (P and Q states, respectively) as bit 1 (see FIG. 4).

In a variation of this embodiment, the variant protein-based memory architecture can be used in the generation of ultra-high density RAMs. These variant protein-based devices offer a comparative advantage over modern-day semiconductors because a 3D system is possible with the variant proteins, the transition from one variant protein state to another occurs more rapidly than currently available electronic systems, and the protein states can readily be converted reversibly back to the state. Moreover, the variant proteins described herein are highly durable and stable to harsh environmental conditions meaning that memory can be generated that provide significant advantages over magnetic and optical data storage devices.

When irradiated with light of the proper wavelength (generally in the 560 to 570 nm region), the variant bacteriorhodopsin undergoes isomerization of the chromophore from an all-trans to a 13-cis configuration, producing a trappable intermediate labeled K, shown in FIG. 10. The proton-pumping mechanism is then performed via a series of dark reactions that form, in succession, the L, M, N and O intermediates (see FIG. 10). In the non-mutated bacteriorhodopsin, the net result is transfer of a proton to the extracellular surface from a series of residues including Arg-82, Glu-194, Glu-204 and Asp-212 (see FIGS. 1, 2, and 3) and a hydrogen-bond network originating from water molecules (collectively referred to as the 'leaving group' or 'XH'—not shown). Replacement of Asp-96 with Asn (D96N) lowers the efficiency of the re-protonation step and increases the lifetime of the M intermediate from a few milliseconds (ms) to 100 ms at ambient temperature. The D96N mutant has been used for real-time holographic memories. The branching reaction that has been used in the operation of 3D memory is shown in FIG. 12. The branch in a two photon process involves (a) light induced activation of the resting state with green light to form the O state and (b) photoactivation of the O state by red light, which induces an all-trans to 9-cis photochemistry transition (see FIG. 10). In a single photon process, photoactivation of the resting state of the protein results in the isomerization of the all-trans retinal to the 9-cis form producing the permanent Q state. The 9-cis chromophore is not stable in the binding site, however, and hydrolysis of the Schiff base takes place to produce 9-cis retinal trapped in the binding site. The result is the formation of the Q state ($\lambda_{max} \approx 380$ nm). In the absence of blue light or high temperatures, data stored using the Q state is stable for decades. However, under blue light irradiation, isomerization of the protein-constrained 9-cis retinal chromophore takes place to generate the all-trans retinal, which spontaneously recombines with Lys-216 to regenerate the light-adapted resting state, bR (see FIGS. 4 and 10).

Thus, in an embodiment, the bacteriorhodopsin variants enhance the efficiency of the branching reaction for use of the protein in device applications. Before examining the variant proteins, devices, methods and procedures provided herein, a discussion of the branched-photocycle optical architecture is useful and provided below.

Branched-photocycle optical data storage 3D memories store information in a volumetric memory medium and offer a 300-fold improvement in data storage capacity for a given enclosure size. The branched-photocycle architecture offers some important advantages. First, it allows the use of two temporally separate beams to store information. This sequential excitation (two photon process) can rigorously exclude any photochemistry outside the irradiated volume, simplifying the optical design and improving reliability (compared to for example compounds that fluoresce). Second, the use of linear, rather than nonlinear, excitation allows the use of inexpensive continuous wave (CW) lasers, which increases flexibility and decreases the cost of the read-write architecture. See FIGS. 4 and 5.

The total memory system of the bacteriorhodopsin variants provided herein gains additional comparative advantage from the inherently low cost of the storage medium. Large quantities of the protein can be produced through simple fermentation and isolation procedures once the mutant is identified. The branching reaction of interest was discussed above and is shown in FIG. 4. In an embodiment, the memory functions by assigning the resting state (bR) to bit 0 and both P and Q to bit 1 (see FIG. 4). The P 'state' is actually a pair of states with absorption maxima at 445 and 525 nm (not shown in the figures) that interconverts rapidly owing to protein relaxation processes. For data storage, these species can be treated as a single intermediate. The above read, write and erase scheme can be realized using the optical layout shown in FIG. 6. In a variation of an embodiment, the device provides a method of storing and retrieving data within a volumetric memory medium consisting of bacteriorhodopsin in a polymer matrix sealed in a plastic cuvette (see for example FIG. 6A). Genetic engineering is used to optimize the protein with respect to maximizing the efficiency of the branching reaction shown in FIG. 4.

Various methods can be used to enhance the yield of the O state and the quantum efficiency of the O to P photoreaction. Note that the O state and bit 0 are different entities (see FIG. 4). Bacteriorhodopsin is optimized in a plurality of ways, such as by chemical modification of the chromophore and/or genetic and/or chemical modification of the protein.

In an embodiment, additional mutants are generated by performing studies in the absence of chromophore or the bacterio-opsin (BO) polypeptide. When the system is deficient in retinal, one can produce BO without incorporating a chromophore and provide an efficient method of generating analogue proteins with synthetically modified chromophores. The use of a BO-deficient cell line also aids in this process. The BO-deficient cell line contains a DNA insertion within the gene that encodes BO, namely "bop". The production of native bacteriorhodopsin is abolished in many BO-deficient cell lines, allowing the expression of mutant proteins. In a variation of this embodiment, strains in which the bop gene is deleted or replaced with a selectable marker are also useful for genetic modification of bacteriorhodopsin. [See Peck, R. F. et al. Homologous gene knockout in the archaeon *Halobacterium salinarum* with ura3 as a counter-selectable marker. *Mol. Microbiol.* 35, 667-676, (2000)]. The principal approaches to genetic engineering of proteins for device applications are site-directed mutagenesis, semi-random mutagenesis, random mutagenesis, directed evolution type I, and directed evolution type II.

FIG. 11 depicts the potential outcomes of optimizing a protein for device applications. Depending on the characteristics being measured several results are possible. Assuming that a triple mutant confers the optimal protein, a single mutation (such as, for example, peak B as shown in FIG. 11*a*) might provide significant improvement. However, the optimal protein (peak E in FIG. 11*a*) might be surrounded by double-mutant troughs because of interference effects. These tend to be very common when the mutations of the key residues involve charged residues.

Site-Directed Mutagenesis

The ability to express bacteriorhodopsin and its site-directed mutants within the native organism, *H. salinarum*, was used in materials optimization. The native organism provided the cellular machinery to express the protein within the purple membrane, and the crystalline lattice of the purple membrane conferred the high photochemical and thermal stability that characterizes this system. Site directed mutagenesis for Q state formation should affect five variables simultaneously: the formation time of O state (wherein it is desired that this state be minimized), the decay of O state (optimize this state), the quantum efficiency of the O to P photochemical transformation (one desires to maximize this transformation), the efficiency of the P to Q hydrolysis (maximize this hydrolysis) and the lifetime of the Q state (maximize this lifetime). Without modeling and/or experimental work, it is difficult to predict which single, double, or triple mutations will accomplish all of these tasks simultaneously. Complex systems (such as the memory) have many variables, which makes optimization by site-directed mutagenesis alone difficult. In this light, one variable of importance to the memory was optimized based on modeling. A series of mutations were constructed involving Glu-194 and Glu-204, both of which have been shown to be important participants in the photocycle.

In an embodiment, other amino acids were demonstrated to be important participants in the photocycle. These include Val-49, Arg-82, Asp-85, Thr-90, Asp-96, Asp-115, Ile-119, Thr-121, Ala-126, Tyr-185, Glu-194, Ala-196, Ile-198, Pro-200, Asn-202, Glu-204, Thr-205, Leu-206, Phe-208, and Asp-212. Thus, in an embodiment, the bacteriorhodopsin variants are selected from the group consisting of V49X, R82X, D85X, T90X, D96X, D115X, I119X, T121X, A126X, Y185X, E194X, A196X, I198X, P200X, N202X, E204X, T205X, L206X, F208X, D212X, wherein X can be any amino acid that is not the same as the amino acid being replaced.

In an embodiment, when the variant is E194X, the variant is not E194Q or E194C. When the variant is E204X, the variant is not E204Q or E204C. When the variant is F208X, the variant is not F208N.

In an alternate embodiment, the variants may have two sites at which site directed mutagenesis has occurred. In a variation, the bacteriorhodopsin variants are selected from the group consisting of V49X/R82X, V49X/D85X, V49X/T90X, V49X/D96X, V49X/D115X, V49X/I119X, V49X/T121X, V49X/A126X, V49X/Y185X, V49X/E194X, V49X/A196X, V49X/I198X, V49X/P200X, V49X/N202X, V49X/E204X, V49X/T205X, V49X/L206X, V49X/F208X, V49X/D212X, R82X/D85X, R82X/T90X, R82X/D96X, R82X/D115X, R82X/119X, R82X/T121X, R82X/A126X, R82X/Y185X, R82X/E194X, R82X/A196X, R82X/198X, R82X/P200X, R82X/N202X, R82X/E204X, R82X/T205X, R82X/L206X, R82X/F208X, R82X/D212X, D85X/T90X, D85X/D96X, D85X/D115X, D85X/I119X, D85X/T121X, D85X/A126X, D85X/Y185X, D85X/E194X, D85X/A196X, D85X/I198X, D85X/P200X, D85X/N202X, D85X/E204X, D85X/T205X, D85X/L206X, D85X/F208X, D85X/D212X, T90X/D96X, T90X/D115X, T90X/I119X, T90X/T121X, T90X/A126X, T90X/Y185X, T90X/E194X, T90X/A196X, T90X/1198X, T90X/P200X, T90X/N202X, T90X/E204X, T90X/T205X, T90X/L206X, T90X/F208X, T90X/D212X, D96X/D115X, D96X/119X, D96X/T121X, D96X/A126X, D96X/Y185X, D96X/E194X, D96X/A196X, D96X/I198X, D96X/P200X, D96X/N202X, D96X/E204X, D96X/T205X, D96X/L206X, D96X/F208X, D96X/D212X, D115X/E194X, D115X/I119X, D115X/T121X, D115X/A126X, D115X/Y185X, D115X/E194X, D115X/A196X, D115X/I198X, D115X/P200X, D115X/N202X, D115X/E204X, D115X/T205X, D115X/L206X, D115X/F208X, D115X/D212X, I119X/T121X, I119X/A126X, I119X/Y185X, I119X/E194X, I119X/A196X, I119X/I198X, I119X/P200X, I119X/N202X, I119X/E204X, I119X/T205X, I119X/L206X, I119X/F208X, I119X/D212X, T121X/A126X, T121X/Y185X, T121X/E194X, T121X/A196X, T121X/I198X, T121X/P200X, T121X/N202X, T121X/E204X, T121X/T205X, T121X/L206X, T121X/F208X, T121X/D212X, A126X/Y185X, A126X/E194X, A126X/A196X, A126X/I198X, A126X/P200X, A126X/N202X, A126X/E204X, A126X/T205X, A126X/L206X, A126X/F208X, A126X/D212X, Y185X/E194X, Y185X/A196X, Y185X/I198X, Y185X/P200X, Y185X/N202X, Y185X/E204X, Y185X/T205X, Y185X/L206X, Y185X/F208X, Y185X/D212X, E194X/A196X, E194X/I198X, E194X/P200X, E194X/N202X, E194X/E204X, E194X/T205X, E194X/L206X, E194X/F208X, E194X/D212X, A196X/I198X, A196X/P200X, A196X/N202X, A196X/E204X, A196X/T205X, A196X/L206X, A196X/F208X, A196X/D212X, I198X/P200X, I198X/N202X, I198X/E204X, I198X/T205X, I198X/L206X, I198X/F208X, I198X/D212X, P200X/N202X, P200X/E204X, P200X/T205X, P200X/L206X, P200X/F208X, P200X/D212X, N202X/E204X, N202X/T205X, N202X/L206X, N202X/F208X, N202X/D212X, E204X/T205X, E204X/L206X, E204X/F208X, E204X/D212X, T205X/L206X, T205X/F208X, T205X/D212X, L206X/F208X, L206X/D212X, and F208X/D212X.

In an alternate embodiment, the variants can have three site directed mutagenesis sites. In a variation, the variants are selected from the group consisting of V49X/R82X/D85X, V49X/R82X/T90X, V49X/R82X/D96X, V49X/R82X/D115X, V49X/R82X/I119X, V49X/R82X/T121X, V49X/R82X/A126X, V49X/R82X/Y185X, V49X/R82X/E194X, V49X/R82X/A196X, V49X/R82X/198X, V49X/R82X/P200X, V49X/R82X/N202X, V49X/R82X/E204X, V49X/R82X/T205X, V49X/R82X/L206X, V49X/R82X/F208X, V49X/R82X/D212X, V49X/D85X/T90X, V49X/D85X/D96X, V49X/D85X/D115X, V49X/D85X/I119X, V49X/D85X/T121X, V49X/D85X/A126X, V49X/D85X/Y185X, V49X/D85X/E194X, V49X/D85X/A196X, V49X/D85X/198X, V49X/D85X/P200X, V49X/D85X/N202X, V49X/D85X/E204X, V49X/D85X/T205X, V49X/D85X/L206X, V49X/D85X/F208X, V49X/D85X/D212X, V49X/T90X/D96X, V49X/T90X/D115X, V49X/T90X/T119X, V49X/T90X/T121X, V49X/T90X/A126X, V49X/T90X/Y185X, V49X/T90X/E194X, V49X/T90X/A196X, V49X/T90X/I198X, V49X/T90X/P200X, V49X/T90X/N202X, V49X/T90X/E204X, V49X/T90X/T205X, V49X/T90X/L206X, V49X/T90X/F208X, V49X/T90X/D212X, V49X/D96X/D115X, V49X/D96X/I119X, V49X/D96X/T121X, V49X/D96X/A126X, V49X/D96X/Y185X, V49X/D96X/E194X, V49X/D96X/A196X, V49X/D96X/I198X, V49X/D96X/P200X, V49X/D96X/N202X, V49X/D96X/E204X, V49X/D96X/T205X, V49X/D96X/L206X, V49X/D96X/F208X, V49X/D96X/D212X, V49X/D115X/I119X, V49X/D115X/T121X, V49X/D115X/A126X, V49X/D115X/Y185X, V49X/D115X/E194X, V49X/D115X/A196X, V49X/D115X/I198X, V49X/D115X/P200X, V49X/D115X/N202X, V49X/D115X/E204X, V49X/D115X/T205X, V49X/D115X/L206X, V49X/D115X/F208X, V49X/D115X/D212X, V49X/I119X/T121X, V49X/I119X/A126X, V49X/I119X/Y185X, V49X/I119X/194X, V49X/I119X/A196X, V49X/I119X/I198X, V49X/I119X/P200X, V49X/I119X/N202X, V49X/I119X/E204X, V49X/I119x/T205X, V49X/I119X/L206X, V49X/I119X/F208X, V49X/I119X/D212X, V49X/T121X/A126X, V49X/T121X/Y185X, V49X/T121X/E194X, V49X/T121X/A196X, V49X/T121X/198X, V49X/T121X/P200X, V49X/T121X/N202X, V49X/T121X/E204X, V49X/T121X/T205X, V49X/T121X/L206X, V49X/T121X/F208X, V49X/T121X/D212X, V49X/A126X/Y185X, V49X/A126X/E194X, V49X/A126X/A196X, V49X/A126X/198X, V49X/A126X/P200X, V49X/A126X/N202X, V49X/A126X/E204X, V49X/A126X/T205X, V49X/A126X/L206X, V49X/A126X/F208X, V49X/A126X/D212X, V49X/Y185X/194X, V49X/Y185X/A196X, V49X/Y185X/198X, V49X/Y185X/P200X, V49X/Y185X/N202X, V49X/Y185X/E204X, V49X/Y185X/T205X, V49X/Y185X/L206X, V49X/Y185X/F208X, V49X/Y185X/D212X, V49X/E194X/A196X, V49X/E194X/I198X, V49X/E194X/P200X, V49X/E194X/N202X, V49X/E194X/E204X, V49X/E194X/T205X, V49X/E194X/L206X, V49X/E194X/F208X, V49X/E194X/D212X, V49X/A196X/198X, V49X/A196X/P200X, V49X/A196X/N202X, V49X/A196X/E204X, V49X/A196X/

T205X, V49X/A196X/L206X, V49X/A196X/F208X, V49X/A196X/D212X, V49X/I198X/P200X, V49X/I198X/N202X, V49X/I198X/E204X, V49X/I198X/T205X, V49X/I198X/L206X, V49X/I198X/F208X, V49X/I198X/D212X, V49X/P200X/N202X, V49X/P200X/E204X, V49X/P200X/T205X, V49X/P200X/L206X, V49X/P200X/F208X, V49X/P200X/D212X, V49X/N202X/E204X, V49X/N202X/T205X, V49X/N202X/L206X, V49X/N202X/F208X, V49X/N202X/D212X, V49X/E204X/T205X, V49X/E204X/L206X, V49X/E204X/F208X, V49X/E204X/D212X, V49X/T205X/L206X, V49X/T205X/F208X, V49X/T205X/D212X, V49X/L206X/F208X, V49X/L206X/D212X, and V49X/F208X/D212X.

In an alternate embodiment, the variants are selected from the group consisting of R82X/D85X/T90X, R82X/D85X/D96X, R82X/D85X/D115X, R82X/D85X/I119X, R82X/D85X/T121X, R82X/D85X/A126X, R82X/D85X/Y185X, R82X/D85X/I94X, R82X/D85X/A196X, R82X/D85X/I198X, R82X/D85X/P200X, R82X/D85X/N202X, R82X/D85X/E204X, R82X/D85X/T205X, R82X/D85X/L206X, R82X/D85X/F208X, R82X/D85X/D212X, R82X/T90X/D96X, R82X/T90X/D115X, R82X/T90X/I119X, R82X/T90X/T121X, R82X/T90X/A126X, R82X/T90X/Y185X, R82X/T90X/I94X, R82X/T90X/A196X, R82X/T90X/I198X, R82X/T90X/P200X, R82X/T90X/N202X, R82X/T90X/E204X, R82X/T90X/T205X, R82X/T90X/L206X, R82X/T90X/F208X, R82X/T90X/D212X, R82X/D96X/D115X, R82X/D96X/I119X, R82X/D96X/T121X, R82X/D96X/A126X, R82X/D96X/Y185X, R82X/D96X/I94X, R82X/D96X/A196X, R82X/D96X/I198X, R82X/D96X/P200X, R82X/D96X/N202X, R82X/D96X/E204X, R82X/D96X/T205X, R82X/D96X/L206X, R82X/D96X/F208X, R82X/D96X/D212X, R82X/D115X/I119X, R82X/D115X/T121X, R82X/D115X/A126X, R82X/D115X/Y185X, R82X/D115X/E194X, R82X/D115X/A196X, R82X/D115X/I198X, R82X/D115X/P200X, R82X/D115X/N202X, R82X/D115X/E204X, R82X/D115X/T205X, R82X/D115X/L206X, R82X/D115X/F208X, R82X/D115X/D212X, R82X/I119X/T121X, R82X/I119X/A126X, R82X/I119X/Y185X, R82X/I119X/I94X, R82X/I119X/A196X, R82X/I119X/I198X, R82X/I119X/P200X, R82X/I119X/N202X, R82X/I119X/E204X, R82X/I19x/T205X, R82X/I119X/L206X, R82X/I119X/F208X, R82X/I119X/D212X, R82X/T121X/A126X, R82X/T121X/Y185X, R82X/T121X/E194X, R82X/T121X/A196X, R82X/T121X/I198X, R82X/T121X/P200X, R82X/T121X/N202X, R82X/T121X/E204X, R82X/T121X/T205X, R82X/T121X/L206X, R82X/T121X/F208X, R82X/T121X/D212X, R82X/A126X/Y185X, R82X/A126X/E194X, R82X/A126X/A196X, R82X/A126X/I198X, R82X/A126X/P200X, R82X/A126X/N202X, R82X/A126X/E204X, R82X/A126X/T205X, R82X/A126X/L206X, R82X/A126X/F208X, R82X/A126X/D212X, R82X/Y185X/I94X, R82X/Y185X/A196X, R82X/Y185X/I198X, R82X/Y185X/P200X, R82X/Y185X/N202X, R82X/Y185X/E204X, R82X/Y185X/T205X, R82X/Y185X/L206X, R82X/Y185X/F208X, R82X/Y185X/D212X, R82X/I94X/A196X, R82X/I94X/I198X, R82X/I94X/P200X, R82X/I94X/N202X, R82X/I94X/E204X, R82X/I94X/T205X, R82X/I94X/L206X, R82X/I94X/F208X, R82X/I94X/D212X, R82X/A196X/I198X, R82X/A196X/P200X, R82X/A196X/N202X, R82X/A196X/E204X, R82X/A196X/T205X, R82X/A196X/L206X, R82X/A196X/F208X, R82X/A196X/D212X, R82X/I198X/P200X, R82X/I198X/N202X, R82X/I198X/E204X, R82X/I198X/T205X, R82X/I198X/L206X, R82X/I198X/F208X, R82X/I198X/D212X, R82X/P200X/N202X, R82X/P200X/E204X, R82X/P200X/T205X, R82X/P200X/L206X, R82X/P200X/F208X, R82X/P200X/D212X, R82X/N202X/E204X, R82X/N202X/T205X, R82X/N202X/L206X, R82X/N202X/F208X, R82X/N202X/D212X, R82X/E204X/T205X, R82X/E204X/L206X, R82X/E204X/F208X, R82X/E204X/D212X, R82X/T205X/L206X, R82X/T205X/F208X, R82X/T205X/D212X, R82X/L206X/F208X, R82X/L206X/D212X, and R82X/F208X/D212X.

In an alternate embodiment, the variants are selected from the group consisting of D85X/T90X/D96X, D85X/T90X/D115X, D85X/T90X/I119X, D85X/T90X/T121X, D85X/T90X/A126X, D85X/T90X/Y185X, D85X/T90X/I94X, D85X/T90X/A196X, D85X/T90X/I198X, D85X/T90X/P200X, D85X/T90X/N202X, D85X/T90X/E204X, D85X/T90X/T205X, D85X/T90X/L206X, D85X/T90X/F208X, D85X/T90X/D212X, D85X/D96X/D115X, D85X/D96X/I119X, D85X/D96X/T121X, D85X/D96X/A126X, D85X/D96X/Y185X, D85X/D96X/I94X, D85X/D96X/A196X, D85X/D96X/I198X, D85X/D96X/P200X, D85X/D96X/N202X, D85X/D96X/E204X, D85X/D96X/T205X, D85X/D96X/L206X, D85X/D96X/F208X, D85X/D96X/D212X, D85X/D115X/I119X, D85X/D115X/T121X, D85X/D115X/A126X, D85X/D115X/Y185X, D85X/D115X/E194X, D85X/D115X/A196X, D85X/D115X/I198X, D85X/D115X/P200X, D85X/D115X/N202X, D85X/D115X/E204X, D85X/D115X/T205X, D85X/D115X/L206X, D85X/D115X/F208X, D85X/D115X/D212X, D85X/I119X/T121X, D85X/I119X/A126X, D85X/I119X/Y185X, D85X/I119X/E194X, D85X/I119X/A196X, D85X/I119X/I198X, D85X/I119X/P200X, D85X/I119x/N202X, D85X/I119X/E204X, D85X/I119X/T205X, D85X/I119X/L206X, D85X/I119X/F208X, D85X/I119X/D212X, D85X/T121X/A126X, D85X/T121X/Y185X, D85X/T121X/E194X, D85X/T121X/A196X, D85X/T121X/I198X, D85X/T121X/P200X, D85X/T121X/N202X, D85X/T121X/E204X, D85X/T121X/T205X, D85X/T121X/L206X, D85X/T121X/F208X, D85X/T121X/D212X, D85X/A126X/Y185X, D85X/A126X/E194X, D85X/A126X/A196X, D85X/A126X/I198X, D85X/A126X/P200X, D85X/A126X/N202X, D85X/A126X/E204X, D85X/A126X/T205X, D85X/A126X/L206X, D85X/A126X/F208X, D85X/A126X/D212X, D85X/Y185X/E194X, D85X/Y185X/A196X, D85X/Y185X/I198X, D85X/Y185X/P200X, D85X/Y185X/N202X, D85X/Y185X/E204X, D85X/Y185X/T205X, D85X/Y185X/L206X, D85X/Y185X/F208X, D85X/Y185X/D212X, D85X/E194X/A196X, D85X/I94X/I198X, D85X/I94X/P200X, D85X/I94X/N202X, D85X/I94X/E204X, D85X/I94X/T205X, D85X/I94X/L206X, D85X/I94X/F208X, D85X/I94X/D212X, D85X/A196X/I198X, D85X/A196X/P200X, D85X/A196X/N202X, D85X/A196X/E204X, D85X/A196X/T205X, D85X/A196X/L206X, D85X/A196X/F208X, D85X/A196X/D212X, D85X/I198X/P200X, D85X/I198X/N202X, D85X/I198X/E204X, D85X/I198X/T205X, D85X/I198X/L206X, D85X/I198X/F208X, D85X/I198X/D212X, D85X/P200X/N202X, D85X/P200X/E204X, D85X/P200X/T205X, D85X/P200X/L206X, D85X/P200X/F208X, D85X/P200X/D212X, D85X/N202X/E204X, D85X/N202X/T205X, D85X/N202X/L206X, D85X/N202X/F208X, D85X/N202X/D212X, D85X/E204X/T205X, D85X/E204X/L206X, D85X/E204X/F208X, D85X/E204X/D212X, D85X/T205X/L206X, D85X/T205X/F208X, D85X/T205X/D212X, D85X/L206X/F208X, D85X/L206X/D212X, and D85X/F208X/D212X.

In an alternate embodiment, the variants are selected from the group consisting of T90X/D96X/D115X, T90X/D96X/I119X, T90X/D96X/T121X, T90X/D96X/A126X, T90X/D96X/Y185X, T90X/D96X/E194X, T90X/D96X/A196X, T90X/D96X/I98X, T90X/D96X/P200X, T90X/D96X/N202X, T90X/D96X/E204X, T90X/D96X/T205X, T90X/D96X/L206X, T90X/D96X/F208X, T90X/D96X/D212X, T90X/D115X/I119X, T90X/D115X/T121X, T90X/D115X/A126X, T90X/D115X/Y185X, T90X/D115X/E194X, T90X/D115X/A196X, T90X/D115X/I198X, T90X/D115X/P200X, T90X/D115X/N202X, T90X/D115X/E204X, T90X/D115X/T205X, T90X/D115X/L206X, T90X/D115X/F208X, T90X/D115X/D212X, T90X/I119X/T121X, T90X/I119X/A126X, T90X/I119X/Y185X, T90X/I119X/E194X, T90X/I119X/A196X, T90X/I119X/I198X, T90X/I119X/P200X, T90X/I119X/N202X, T90X/I119X/E204X, T90X/I119X/T205X, T90X/I119X/L206X, T90X/I119X/F208X, T90X/I119X/D212X, T90X/T121X/A126X, T90X/T121X/Y185X, T90X/T121X/E194X, T90X/T121X/A196X, T90X/T121X/I198X, T90X/T121X/P200X, T90X/T121X/N202X, T90X/T121X/E204X, T90X/T121X/T205X, T90X/T121X/L206X, T90X/T121X/F208X, T90X/T121X/D212X, T90X/A126X/Y185X, T90X/A126X/E194X, T90X/A126X/A196X, T90X/A126X/I198X, T90X/A126X/P200X, T90X/A126X/N202X, T90X/A126X/E204X, T90X/A126X/T205X, T90X/A126X/L206X, T90X/A126X/F208X, T90X/A126X/D212X, T90X/Y185X/I94X, T90X/Y185X/A196X, T90X/Y185X/I98X, T90X/Y185X/P200X, T90X/Y185X/N202X, T90X/Y185X/E204X, T90X/Y185X/T205X, T90X/Y185X/L206X, T90X/Y185X/F208X, T90X/Y185X/D212X, T90X/E194X/A196X, T90X/E194X/I98X, T90X/E194X/P200X, T90X/E194X/N202X, T90X/E194X/E204X, T90X/E194X/T205X, T90X/E194X/L206X, T90X/E194X/F208X, T90X/E194X/D212X, T90X/A196X/I98X, T90X/A196X/P200X, T90X/A196X/N202X, T90X/A196X/E204X, T90X/A196X/T205X, T90X/A196X/L206X, T90X/A196X/F208X, T90X/A196X/D212X, T90X/I198X/P200X, T90X/I198X/N202X, T90X/I198X/E204X, T90X/I198X/T205X, T90X/I198X/L206X, T90X/I198X/F208X, T90X/I198X/D212X, T90X/P200X/N202X, T90X/P200X/E204X, T90X/P200X/T205X, T90X/P200X/L206X, T90X/P200X/F208X, T90X/P200X/D212X, T90X/N202X/E204X, T90X/N202X/T205X, T90X/N202X/L206X, T90X/N202X/F208X, T90X/N202X/D212X, T90X/E204X/T205X, T90X/E204X/L206X, T90X/E204X/F208X, T90X/E204X/D212X, T90X/T205X/L206X, T90X/T205X/F208X, T90X/T205X/D212X, T90X/L206X/F208X, T90X/L206X/D212X, and T90X/F208X/D212X.

In an alternate embodiment, the variants are selected from the group consisting of D96X/D115X/I119X, D96X/D115X/T121X, D96X/D115X/A126X, D96X/D115X/Y185X, D96X/D115X/E194X, D96X/D115X/A196X, D96X/D115X/I198X, D96X/D115X/P200X, D96X/D 115X/N202X, D96X/D 115X/E204X, D96X/D115X/T205X, D96X/D 115X/L206X, D96X/D115X/F208X, D96X/D115X/D212X, D96X/I119X/T121X, D96X/I119X/A126X, D96X/I119X/Y185X, D96X/I119X/E194X, D96X/I119X/A196X, D96X/I119X/I198X, D96X/I119X/P200X, D96X/I119X/N202X, D96X/I119X/E204X, D96X/I119X/T205X, D96X/I119X/L206X, D96X/I119X/F208X, D96X/I119X/D212X, D96X/T121X/A126X, D96X/T121X/Y185X, D96X/T121X/E194X, D96X/T121X/A196X, D96X/T121X/I198X, D96X/T121X/P200X, D96X/T121X/N202X, D96X/T121X/E204X, D96X/T121X/T205X, D96X/T121X/L206X, D96X/T121X/F208X, D96X/T121X/D212X, D96X/A126X/Y185X, D96X/A126X/E194X, D96X/A126X/A196X, D96X/A126X/198X, D96X/A126X/P200X, D96X/A126X/N202X, D96X/A126X/E204X, D96X/A126X/T205X, D96X/A126X/L206X, D96X/A126X/F208X, D96X/A126X/D212X, D96X/Y185X/194X, D96X/Y185X/A196X, D96X/Y185X/198X, D96X/Y185X/P200X, D96X/Y185X/N202X, D96X/Y185X/E204X, D96X/Y185X/T205X, D96X/Y185X/L206X, D96X/Y185X/F208X, D96X/Y185X/D212X, D96X/E194X/A196X, D96X/E194X/I198X, D96X/E194X/P200X, D96X/E194X/N202X, D96X/E194X/E204X, D96X/E194X/T205X, D96X/E194X/L206X, D96X/E194X/F208X, D96X/E194X/D212X, D96X/A196X/198X, D96X/A196X/P200X, D96X/A196X/N202X, D96X/A196X/E204X, D96X/A196X/T205X, D96X/A196X/L206X, D96X/A196X/F208X, D96X/A196X/D212X, D96X/I198X/P200X, D96X/I198X/N202X, D96X/I198X/E204X, D96X/I198X/T205X, D96X/I198X/L206X, D96X/I198X/F208X, D96X/I198X/D212X, D96X/P200X/N202X, D96X/P200X/E204X, D96X/P200X/T205X, D96X/P200X/L206X, D96X/P200X/F208X, D96X/P200X/D212X, D96X/N202X/E204X, D96X/N202X/T205X, D96X/N202X/L206X, D96X/N202X/F208X, D96X/N202X/D212X, D96X/E204X/T205X, D96X/E204X/L206X, D96X/E204X/F208X, D96X/E204X/D212X, D96X/T205X/L206X, D96X/T205X/F208X, D96X/T205X/D212X, D96X/L206X/F208X, D96X/L206X/D212X, and D96X/F208X/D212X.

In an alternate embodiment, the variants are selected from the group consisting of D115X/I119X/T121X, D115X/I119X/A126X, D115X/I119X/Y185X, D115X/I119X/E194X, D115X/I119X/A196X, D115X/I119X/I198X, D115X/I119X/P200X, D115X/I119X/N202X, D115X/I119X/E204X, D115X/I119X/T205X, D115X/I119X/L206X, D115X/I119X/F208X, D115X/I119X/D212X, D115X/T121X/A126X, D115X/T121X/Y185X, D115X/T121X/E194X, D115X/T121X/A196X, D115X/T121X/I198X, D115X/T121X/P200X, D115X/T121X/N202X, D115X/T121X/E204X, D115X/T121X/T205X, D115X/T121X/L206X, D115X/T121X/F208X, D115X/T121X/D212X, D115X/A126X/Y185X, D115X/A126X/E194X, D115X/A126X/A196X, D115X/A126X/I198X, D115X/A126X/P200X, D115X/A126X/N202X, D115X/A126X/E204X, D115X/A126X/T205X, D115X/A126X/L206X, D115X/A126X/F208X, D115X/A126X/D212X, D115X/Y185X/E194X, D115X/Y185X/A196X, D115X/Y185X/I198X, D115X/Y185X/P200X, D115X/Y185X/N202X, D115X/Y185X/E204X, D115X/Y185X/T205X, D115X/Y185X/L206X, D115X/Y185X/F208X, D115X/Y185X/D212X, D115X/E194X/A196X, D115X/E194X/I198X, D115X/E194X/P200X, D115X/E194X/N202X, D115X/E194X/E204X, D115X/E194X/T205X, D115X/E194X/L206X, D115X/E194X/F208X, D115X/E194X/D212X, D115X/A196X/I198X, D115X/A196X/P200X, D115X/A196X/N202X, D115X/A196X/E204X, D115X/A196X/T205X, D115X/A196X/L206X, D115X/A196X/F208X, D115X/A196X/D212X, D115X/I198X/P200X, D115X/I198X/N202X, D115X/I198X/E204X, D115X/I198X/T205X, D115X/I198X/L206X, D115X/I198X/F208X, D115X/I198X/D212X, D115X/P200X/N202X, D115X/P200X/E204X, D115X/P200X/T205X, D115X/P200X/L206X, D115X/P200X/F208X, D115X/P200X/D212X, D115X/N202X/E204X, D115X/N202X/T205X, D115X/N202X/L206X, D115X/N202X/F208X, D115X/N202X/D212X, D115X/E204X/T205X, D115X/E204X/L206X, D115X/E204X/F208X, D115X/E204X/D212X, D115X/T205X/L206X, D115X/T205X/F208X, D115X/T205X/D212X, D115X/L206X/F208X, D115X/L206X/D212X, and D115X/F208X/D212X.

In an alternate embodiment, the variants are selected from the group consisting of I119X/T121X/A126X, I119X/T121X/Y185X, I119X/T121X/E194X, I119X/T121X/A196X, I119X/T121X/I198X, I119X/T121X/P200X, I119X/T121X/N202X, I119X/T121X/E204X, I119X/T121X/T205X, I119X/T121X/L206X, I119X/T121X/F208X, I119X/T121X/D212X, I119X/A126X/Y185X, I119X/A126X/E194X, I119X/A126X/A196X, I119X/A126X/I198X, I119X/A126X/P200X, I119X/A126X/N202X, I119X/A126X/E204X, I119X/A126X/T205X, I119X/A126X/L206X, I119X/A126X/F208X, I119X/A126X/D212X, I119X/Y185X/E194X, I119X/Y185X/A196X, I119X/Y185X/I198X, I119X/Y185X/P200X, I119X/Y185X/N202X, I119X/Y185X/E204X, I119X/Y185X/T205X, I119X/Y185X/L206X, I119X/Y185X/F208X, I119X/Y185X/D212X, I119X/E194X/A196X, I119X/E194X/I198X, 119X/194X/P200X, I119X/E194X/N202X, I119X/E194X/E204X, I119X/E194X/T205X, I119X/E194X/L206X, I119X/E194X/F208X, I119X/194X/D212X, I119X/A196X/I198X, I119X/A196X/P200X, I119X/A196X/N202X, I119X/A196X/E204X, I119X/A196X/T205X, I119X/A196X/L206X, I119X/A196X/F208X, I119X/A196X/D212X, I119X/I198X/P200X, I119X/I198X/N202X, I119X/I198X/E204X, I119X/I198X/T205X, I119X/I198X/L206X, I119X/I198X/F208X, I119X/I198X/D212X, I119X/P200X/N202X, I119X/P200X/E204X, I119X/P200X/T205X, I119X/P200X/L206X, I119X/P200X/F208X, I119X/P200X/D212X, I119X/N202X/E204X, I119X/N202X/T205X, I119X/N202X/L206X, I119X/N202X/F208X, I119X/N202X/D212X, I119X/E204X/T205X, I119X/E204X/L206X, I119X/E204X/F208X, I119X/E204X/D212X, I119X/L206X/F208X, I119x/L206X/D212X, and I119X/F208X/D212X.

In an embodiment, when the variant is I119X/T121X/A126X, the variant is not I119T/T121S/A126T.

In an alternate embodiment, the variants are selected from the group consisting of T121X/A126X/Y185X, T121X/A126X/E194X, T121X/A126X/A196X, T121X/A126X/I198X, T121X/A126X/P200X, T121X/A126X/N202X, T121X/A126X/E204X, T121X/A126X/T205X, T121X/A126X/L206X, T121X/A126X/F208X, T121X/A126X/D212X, T121X/Y185X/E194X, T121X/Y185X/A196X, T121X/Y185X/I198X, T121X/Y185X/P200X, T121X/Y185X/N202X, T121X/Y185X/E204X, T121X/Y185X/T205X, T121X/Y185X/L206X, T121X/Y185X/F208X, T121X/Y185X/D212X, T121X/E194X/A196X, T121X/E194X/I198X, T121X/E194X/P200X, T121X/E194X/N202X, T121X/E194X/E204X, T121X/E194X/T205X, T121X/E194X/L206X, T121X/E194X/F208X, T121X/E194X/D212X, T121X/A196X/I198X, T121X/A196X/P200X, T121X/A196X/N202X, T121X/A196X/E204X, T121X/A196X/T205X, T121X/A196X/L206X, T121X/A196X/F208X, T121X/A196X/D212X, T121X/I198X/P200X, T121X/I198X/N202X, T121X/I198X/E204X, T121X/I198X/T205X, T121X/I198X/L206X, T121X/I198X/F208X, T121X/I198X/D212X, T121X/P200X/N202X, T121X/P200X/E204X, T121X/P200X/T205X, T121X/P200X/L206X, T121X/P200X/F208X, T121X/P200X/D212X, T121X/N202X/E204X, T121X/N202X/T205X, T121X/N202X/L206X, T121X/N202X/F208X, T121X/N202X/D212X, T121X/E204X/T205X, T121X/E204X/L206X, T121X/E204X/F208X, T121X/E204X/D212X, T121X/T205X/L206X, T121X/T205X/F208X, T121X/T205X/D212X, T121X/L206X/F208X, T121X/L206X/D212X, and T121X/F208X/D212X.

In an alternate embodiment, the variants are selected from the group consisting of A126X/Y185X/E194X, A126X/Y185X/A196X, A126X/Y185X/I198X, A126X/Y185X/P200X, A126X/Y185X/N202X, A126X/Y185X/E204X, A126X/Y185X/T205X, A126X/Y185X/L206X, A126X/Y185X/F208X, A126X/Y185X/D212X, A126X/E194X/A196X, A126X/E194X/I198X, A126X/E194X/P200X, A126X/E194X/N202X, A126X/E194X/E204X, A126X/E194X/T205X, A126X/E194X/L206X, A126X/E194X/F208X, A126X/E194X/D212X, A126X/A196X/I198X, A126X/A196X/P200X, A126X/A196X/N202X, A126X/A196X/E204X, A126X/A196X/T205X, A126X/A196X/L206X, A126X/A196X/F208X, A126X/A196X/D212X, A126X/I198X/P200X, A126X/I198X/N202X, A126X/I198X/E204X, A126X/I198X/T205X, A126X/I198X/L206X, A126X/I198X/F208X, A126X/I198X/D212X, A126X/P200X/N202X, A126X/P200X/E204X, A126X/P200X/T205X, A126X/P200X/L206X, A126X/P200X/F208X, A126X/P200X/D212X, A126X/N202X/E204X, A126X/N202X/T205X, A126X/N202X/L206X, A126X/N202X/F208X, A126X/N202X/D212X, A126X/E204X/T205X, A126X/E204X/L206X, A126X/E204X/F208X, A126X/E204X/D212X, A126X/T205X/L206X, A126X/T205X/F208X, A126X/T205X/D212X, A126X/L206X/F208X, A126X/L206X/D212X, and A126X/F208X/D212X.

In an alternate embodiment, the variants are selected from the group consisting of Y185X/E194X/A196X, Y185X/E194X/I198X, Y185X/E194X/P200X, Y185X/E194X/N202X, Y185X/E194X/E204X, Y185X/E194X/T205X, Y185X/E194X/L206X, Y185X/E194X/F208X, Y185X/E194X/D212X, Y185X/A196X/I198X, Y185X/A196X/P200X, Y185X/A196X/N202X, Y185X/A196X/E204X, Y185X/A196X/T205X, Y185X/A196X/L206X, Y185X/A196X/F208X, Y185X/A196X/D212X, Y185X/I198X/P200X, Y185X/I198X/N202X, Y185X/I198X/E204X, Y185X/I198X/T205X, Y185X/I198X/L206X, Y185X/I198X/F208X, Y185X/I198X/D212X, Y185X/P200X/N202X, Y185X/P200X/E204X, Y185X/P200X/T205X, Y185X/P200X/L206X, Y185X/P200X/F208X, Y185X/P200X/D212X, Y185X/N202X/E204X, Y185X/N202X/T205X, Y185X/N202X/L206X, Y185X/N202X/F208X, Y185X/N202X/D212X, Y185X/E204X/T205X, Y185X/E204X/L206X, Y185X/E204X/F208X, Y185X/E204X/D212X, Y185X/T205X/L206X, Y185X/T205X/F208X, Y185X/T205X/D212X, Y185X/L206X/F208X, Y185X/L206X/D212X, and Y185X/F208X/D212X.

In an alternate embodiment, the variants are selected from the group consisting of E194X/A196X/I198X, E194X/A196X/P200X, E194X/A196X/N202X, E194X/A196X/E204X, E194X/A196X/T205X, E194X/A196X/L206X, E194X/A196X/F208X, E194X/A196X/D212X, E194X/I198X/P200X, E194X/I198X/N202X, E194X/I198X/E204X, E194X/I198X/T205X, E194X/I198X/L206X, E194X/I198X/F208X, E194X/I198X/D212X, E194X/P200X/N202X, E194X/P200X/E204X, E194X/P200X/T205X, E194X/P200X/L206X, E194X/P200X/F208X, E194X/P200X/D212X, E194X/N202X/E204X, E194X/N202X/T205X, E194X/N202X/L206X, E194X/N202X/F208X, E194X/N202X/D212X, E194X/E204X/T205X, E194X/E204X/L206X, E194X/E204X/F208X, E194X/E204X/D212X, E194X/T205X/L206X, E194X/T205X/F208X, E194X/T205X/D212X, E194X/L206X/F208X, E194X/L206X/D212X, and E194X/F208X/D212X.

In an alternate embodiment, the variants selected from the group consisting of A196X/I198X/P200X, A196X/I198X/N202X, A196X/I198X/E204X, A196X/I198X/T205X, A196X/I198X/L206X, A196X/I198X/F208X, A196X/I198X/D212X, A196X/P200X/N202X, A196X/P200X/E204X, A196X/P200X/T205X, A196X/P200X/L206X, A196X/P200X/F208X, A196X/P200X/D212X, A196X/N202X/E204X, A196X/N202X/T205X, A196X/N202X/L206X, A196X/N202X/F208X, A196X/N202X/D212X, A196X/E204X/T205X, A196X/E204X/L206X, A196X/

E204X/F208X, A196X/E204X/D212X, A196X/T205X/ L206X, A196X/T205X/F208X, A196X/T205X/D212X, A196X/L206X/F208X, A196X/L206X/D212X, and A196X/ F208X/D212X.

In an alternate embodiment, the variants are selected from the group consisting of I198X/P200X/N202X, I198X/ P200X/E204X, I198X/P200X/T205X, I198X/P200X/ L206X, I198X/P200X/F208X, I198X/P200X/D212X, I198X/N202X/E204X, I198X/N202X/T205X, I198X/ N202X/L206X, I198X/N202X/F208X, I198X/N202X/ D212X, I198X/E204X/T205X, I198X/E204X/L206X, I198X/E204X/F208X, I198X/E204X/D212X, I198X/ T205X/L206X, I198X/T205X/F208X, I198X/T205X/ D212X, I198X/L206X/F208X, I198X/L206X/D212X, and I198X/F208X/D212X.

In an alternate embodiment, the variants are selected from the group consisting of P200X/N202X/E204X, P200X/ N202X/T205X, P200X/N202X/L206X, P200X/N202X/ F208X, P200X/N202X/D212X, P200X/E204X/T205X, P200X/E204X/L206X, P200X/E204X/F208X, P200X/ E204X/D212X, P200X/T205X/L206X, P200X/T205X/ F208X, P200X/T205X/D212X, P200X/L206X/F208X, P200X/L206X/D212X, and P200X/F208X/D212X.

In an alternate embodiment, the variants are selected from the group consisting of N202X/E204X/T205X, N202X/ E204X/L206X, N202X/E204X/F208X, N202X/E204X/ D212X, N202X/T205X/L206X, N202X/T205X/F208X, N202X/T205X/D212X, N202X/L206X/F208X, N202X/ L206X/D212X, and N202X/F208X/D212X.

In an alternate embodiment, the variants are selected from the group consisting of E204X/T205X/L206X, E204X/ T205X/F208X, E204X/T205X/D212X, E204X/L206X/ F208X, E204X/L206X/D212X, and E204X/F208X/D212X.

In an alternate embodiment, the variants are selected from the group consisting of T205X/L206X/F208X, T205X/ L206X/D212X, T205X/F208X/D212X, and L206X/F208X/ D212X.

In an alternate embodiment, the variants contain four site directed mutagenesis sites. In a variation, these four site directed mutagenesis sites are any four of V49X, R82X, D85X, T90X, D96X, D115X, T119X, T121X, A126X, Y185X, E194X, A196X, I198X, P200X, N202X, E204X, T205X, L206X, F208X, and D212X.

In an alternate embodiment, the variants contain five site directed mutagenesis sites. In a variation, these five site directed mutagenesis sites are any five of V49X, R82X, D85X, T90X, D96X, D115X, I119X, T121X, A126X, Y185X, E194X, A196X, I198X, P200X, N202X, E204X, T205X, L206X, F208X, and D212X.

In an alternate embodiment, the variants contain six site directed mutagenesis sites. In a variation, these six site directed mutagenesis sites are any six of V49X, R82X, D85X, T90X, D96X, D115X, I119X, T121X, A126X, Y185X, E194X, A196X, I198X, P200X, N202X, E204X, T205X, L206X, F208X, and D212X.

In all of the enumerated variants, X can be any amino acid that is different from the amino acid that it is replacing. For example, X can be any naturally incorporated amino acid (during translation), such as A, R, N, D, C, Q, E, G, H, I, L, K, M, F, P, S, T, W, Y, or V.

In a variation of this embodiment, X is an amino acid that comprises a conservative amino acid substitution. By conservative amino acid substitution, it is meant that an amino acid molecule with a similar side chain is substituted for the wild-type amino acid. For example, D is considered to be an acidic amino acid and can be replaced by the acidic amino acid E (or alternatively, E can be replaced by D). Similarly, L, with a hydrophobic side chain can be replaced with any of G, A, V, M, F, W or I (or V can be replaced by any of G, A, L, M, F, W or I). Similarly, T can be replaced by S or Y.

In an embodiment, the variants are selected from the group consisting of V49X, L206X, D85X/D96X, E194X, D85X, E204X, T90X/V49X, T90X/V49X/E204X, E204X, D212X/ Y185X, E204X/F208X, E194X/N202X, E204X, I119X/ T121X/A126X, E194X/E204X, E204X, E194X, A196X/ F208X, A196X/I198X/P200X/E204X/T205X/F208X, R82X, T90X, D85X/V49X, F208X, and E204X/T205X/ F208X. In a variation, the variants are selected from the group consisting of V49A, L206P, D85E/D96Q, E194A, D85E, E204Q, T90A/V49A, T90A/V49A/E204Q, E204N, D212N/ Y185F, E204G/F208V, E194A/N202I, E204G, I119T/ T121S/A126T, E194C/E204C, E204C, E194N, A196S/ F208V, A196S/I198L/P200T/E204A/T205Q/F208V, R82A, T90A, D85N/V49A, F208V, and E204A/T205Q/F208V.

The protein variants described herein relied on mutational strategies such as screening and/or selection to achieve the goals (such as optimization of the five variables discussed above). Screening involved inspection of a population for a given characteristic (usually a phenotype of interest) but placed no limits on the viability of the organisms that possessed (or more importantly did not possess) the desired characteristic. When selection was used, a predetermined mechanism allowed only a certain population to survive. One selection process that was used was linking the antibiotic mevinolin to the mutant gene in a plasmid and selecting those colonies that survived growing conditions wherein mevinolin was present. That is, only those colonies that survived were selected as containing the mutant gene.

In other cases, the genetic optimization process was performed by creating random mutations and observing the impact of these mutations on the desired properties. This process required the screening of mutations and determining which mutants were to be used as templates for further exploration. A single random-mutation cycle yielded several mutant proteins with improved properties. In other cases, several or more cycles were performed to achieve a significant improvement. Random mutations in most cases were more likely to be destructive or neutral than constructive. The total number of unique mutations for a protein the size of BR (248 residues) is 4712 single mutations and 11,056,708 double mutations.

For the random mutant studies wherein screening was involved, the process described by You et al., Wan et al. and/or Callahan et al. was followed. [See L. You et al. Directed evolution of subtilisin E in *Bacillus subtilis* to enhance total activity in aqueous dimethylformamide. *Protein Eng.* 9, 719 (1996); L. Wan et al. In vitro evolution of horse heart myoglobin to increase peroxidase activity. *Proc. Natl. Acad. Sci. U.S.A.* 95, 12825-12831 (1998); M. Callahan et al. An efficient random mutagenesis technique using an *E. coli* mutator strain. *Methods Mol. Biol.* 57, 375-385 (1996)]. The net result was a population of mutant proteins with no a priori bias of location in the sequence. Alternatively, a combination of methods was used to generate controlled numbers of randomly distributed mutations.

In a few cases, semi-random mutagenesis was performed wherein site directed and random mutagenesis were combined to achieve high mutagenesis efficiencies over a limited region. The procedure of Bowie et al., Wen et al., Krebs et al. and/or Whaley et al. were followed. [See J. U. Bowie et al. Deciphering the message in protein sequences: tolerance to amino acid substitutions. *Science.* 247, 1306-1310, (1990); J. Wen, et al. Exploring the allowed sequence space of a membrane protein. *Nat. Struct. Biol.* 3, 141-148, (1996); M. P.

Krebs et al. Intramembrane substitutions in helix D of bacteriorhodopsin disrupt the purple membrane. *J. Mol. Biol.* 267, 172-183, (1997); M. P. Krebs et al. Gene replacement in *Halobacterium halobium* and expression of bacteriorhodopsin mutants. *Proc. Natl. Acad. Sci. U.S.A.* 90, 1987-1991, (1993); and S. R. Whaley et al. Selection of peptides with semiconductor binding specificity for directed nanocrystal assembly. *Nature.* 405, 665-668, (2000)]. This methodology was found to be significantly advantageous for bioelectronic optimizations. In one variation of this technique, the complete bop sequence of the bacteriorhodopsin gene was divided into 17 segments of approximately 15 targeted amino acids that were mutated at a high rate without disturbing the surrounding sequence. Mutations were created by PCR using a "doped" primer that is synthesized with a mixture containing 80% of the wild-type nucleotide and 6.6% of each non-wild-type nucleotide at each position within the targeted region. At this doping level, approximately five amino acid substitutions are predicted per mutant, based on Monte Carlo calculations. The doped oligonucleotides were combined with additional primers in a three-step PCR reaction. The resulting mutant bop fragment was digested with restriction enzymes and ligated with plasmid DNA to generate a library of at least 3000 mutant bop genes in *E. coli*. The pooled library was transformed into an *H. salinarum* strain developed specifically for high-efficiency bop mutagenesis, and recombinant colonies containing a single copy of the mutant bop genes were isolated by homologous gene replacement. Because the mutations within the targeted region are random, the recombinant colonies exhibited a range of colors, reflecting a variation in BR spectral properties and expression levels among the mutants. Many purple mutants in four regions of BR were isolated and sequenced at the nucleotide level. An average of 1.2 amino acid substitutions was observed among purple mutants. This value was lower than the expected value of five substitutions per mutant, presumably because a higher number of substitutions interfered with the formation of native BR. To identify variants with potentially improved photonic properties, the purple membrane from semi-random mutants was partially purified in 96-well format by repeated ultracentrifugation. The BR in these samples was then screened for variation in spectral characteristics and photocycle intermediate lifetimes, particularly that of the O intermediate. UV-visible spectra, O state formation and O decay times were collected for each mutant and the Q value was calculated. Despite the fact that these mutants were not developed a priori, some of them show Q values higher than those for site-directed mutants designed using modeling methods and structural information. Previous work showed that the triple mutant I119T/T121S/A126T had a Q value that is ~50% higher than the largest Q value for any site-directed mutant. Site-directed mutagenesis was then used to dissect the contribution of particular residues within this multiple mutant.

Another technique that was used to develop variants was the use of directed evolution and combinatorial methods. In these experiments, one begins with wild-type protein that has become efficient for its intended purpose through evolution. A key challenge in using directed evolution for materials optimization is establishing a selection method that focuses on the desired properties of the material generated by the host. The use of directed evolution may not guarantee the creation of the ultimate material because the number of possible mutations and the time it takes to explore all the possibilities is years if not decades long. But directed evolution does provide a method of exploring a large number of possible mutations in a systematic way which yields the highest probability of improving the properties of a biological material.

Directed evolution can be divided into two types: Type I and II, neither of which are discrete but rather represent a continuum of procedures that start with screening and end with selection. The major difference between Type I and Type II directed evolution is the level at which the screening or selection is implemented. Type I includes protein screening at the colony or protein level, whereas Type II includes screening or selection of BR in individual cells. Both methods entail identifying proteins with the highest Q values and using these mutants in the next round of screening (see FIG. 11). Type I directed evolution involves screening of large numbers of colonies using a multi-well plate, or other high-throughput screening method. Because *H. salinarum* cells burst when placed in water, colonies can be placed in small aliquots of water and screened in the same 96-well plate format as would be done with isolated protein. Direct screening on colonies of *H. salinarum* avoids the need for protein isolation but at the cost of introducing more scattering to the sample. Type II directed evolution deals with detection of optimized forms at the microscopic organismal level and represents a very powerful technique. Screening and selection are used in tandem. A population of *H. salinarum* cells passes through an automated screening device comprising laser diodes and a charge couple device (CCD) detector array. This device is essentially identical to the write process in the memory. The cells that show the most conversion to P and Q states (as monitored by a concomitant loss of the O state) are separated from other cells and shunted to a collection vessel.

The bop gene sequence from these cells is obtained using in vivo PCR, and favorable mutations are used for the next round of optimization. Type II directed evolution is more efficient than Type I but is more difficult to implement. Because individual organisms are being monitored, cell to cell variation is problematic. In Type I directed evolution this variation is accounted for by looking at thousands of organisms or protein patches simultaneously. However, Type II directed evolution often gives superior results. The Type II directed evolution generally provides the greatest possibility for high-throughput detection of the mutant that is best optimized for device applications.

The extent to which the variation in a population increases is dictated by the choice of the mutagenesis method. Site-directed mutagenesis can be used to explore small changes by changing one residue, and in the absence of structural information about the protein, can be used to fine-tune a particular mutant. However, there are instances wherein the modification of one amino acid provides greatly superior advantages to the un-mutated construct. In an embodiment, existing site-directed mutants can be combined with mutants found in Type I and Type II screening and selection. In a variation of this embodiment, mutants at the Glu194 and Glu204 can be combined with other mutants in an attempt to combine favorable properties from different sources.

Although site directed mutagenesis sometimes provides useful results, other techniques can be used that may be designed to explore a greater area of the mutational landscape for a given protein. For example, the semi-random mutagenesis technique samples a mutational space that is greater compared to site-directed mutagenesis. The sampling of this space means that a new optimum might be reached instead of continuing to improve an original optimization (as in site directed mutagenesis). In this regard, random mutagenesis presents simultaneous advantages and disadvantages: it can be used to find new regions in the protein for optimization, but at the cost of neglecting the original optimization unless randomized libraries incorporating the desired mutation are used. The strategies for optimizing photochemical properties generally should take into account the localized nature of the mutational landscape. However, once key regions for mutagenesis are discovered, semi-random mutagenesis or site directed mutagenesis provides the most productive approach.

Accordingly, the present method relates to the use of the genetically optimized bacteriorhodopsin variants in optical memory storage processors. A major consideration in the use of the branched photocycle architecture is a photoactive protein. The photoactive protein, upon light activation, should be capable of forming non-volatile stable photointermediate states. The optical storage device of the present method employs laser beams for the processes of reading and writing. The BR variants as enumerated in the present method are efficient Q-state formers and have implications in the development of a new generation of ultra-high speed RAMs. Although wild-type BR has been applied for its role in memory storage devices, the mutants provided herein are superior memory storage devices.

Bacteriorhodopsin is an integral membrane protein found in the cell membrane of *Halobacterium salinarum*, an archaea native to hyper-saline environments. This archaea inhabits salt marshes where the salt concentration is roughly six times that of sea water (>5M NaCl). Bacteriorhodopsin expression in *H. salinarum* is stimulated under low oxygen and high light intensities. The BR molecule assembles into a two-dimensional crystalline lattice (2D) of trimers forming the purple membrane (PM). Purple membrane containing BR is in close association with membrane lipids that are useful for protein structure, function and stability. The light absorption by bacteriorhodopsin results in proton pumping concomitant with the generation of a chemiosmotic membrane potential that is used as an energy source (ATP). Bacteriorhodopsin is composed of a protein component (opsin bound to the prosthetic group), and an all-trans retinal attached to the protein component via a protonated Schiff base linkage (linked to a conserved lysine residue in helix G of the protein component). The positive charge associated with the chromophore interacts electrostatically with the negatively charged counterion complex that is present in the protein component (Asp 85 and Asp 212) in the protein binding site. Absorption of light by the protein causes a rotation around the C13-C14 double bond in the chromophore. This process, termed photoisomerization is completed in less than one picosecond (10-12 seconds). The change in the chromophore conformation is associated with the movement of electrons down the polyene chain towards the protonated Schiff base linkage. The movement of charge down the polyene chain results in the generation of fast photoelectric voltage with a rise-time of less than 5 picoseconds. Changes in the chromophore conformation is associated with corresponding changes in the protein microenvironment that is relayed as spectrally discrete photointermediate states constituting the primary photocycle (K, L, M, N and O). The branched photocycle in wild-type BR occurs as a branch-off reaction via a sequential one-photon process (two-photon) from the O-state. This alternate pathway is characterized by the short-lived P-state and a Q-state that is stable for up to twelve years (see for example, FIG. 4). It is the branched photochemistry of BR that makes it possible to optically write, read, and erase data from the protein. The hexagonal arrangement of the protein in the purple membrane provides the protein with extreme thermal and photochemical stability. Protein denaturation occurs at high temperatures and in severe chemical environments. The high cyclicity (number of times the molecule can be switched between states) and quantum efficiency index (0.65) of bacteriorhodopsin far exceeds that of any synthetic non-native photochromic material.

Thus, in an embodiment, the intrinsic stability and sensitivity of BR makes it useful in device applications. It has been discovered that genetically engineered variants of bacteriorhodopsin with amino acid substitutions at positions: V49X, R82X, D85X, T90X, D96X, D115X, I119X, T121X, A126X, E204X, E194X, A196X, I198X, P200X, N202X, E204X, T205X, L206X, F208X, D212X, and combinations thereof (wherein the first letter represents the amino acid at the respective amino acid position and X represents the mutant amino acid—as described in more detail above) have resulted in the generation of BR variants with enhanced photochromic properties. These BR variants have been identified as excellent data storage materials with increased sensitivity. In the branched photocycle memory architecture described herein, the branching occurs via a single one-photon process and or a two photon process increasing the read/write efficiency.

Activation and data writing onto a specific region in the cube prevents any unwanted photochemistry thus increasing the writing sensitivity. The description of an ideal representation of the 3D memory storage device capable of write/read/erase process is as follows: Paging the BR variant-containing cubes with red light causes the conversion of specific volumes within the irradiated cube to form the P state that thermally relaxes to form the stable Q state via a single photon process. This process is associated with the act of writing data onto specific regions in the volumetric 3D memory. Paging the memory cube with low powered red light provides the capability of differential absorptivity that aids in distinguishing the paged from the unpaged regions of the cube, which is actively projected onto a CCD detector. Illumination of the volumetric 3D memory cube with blue light efficiently restores the resting state and is associated with the erase process (depicted in FIGS. 6 and 7). A detailed description of the 3D memory architecture, wherein the branching occurs via a two photon process, is described in U.S. Pat. No. 5,253,198.

The genetically engineered BR variants provided herein form the permanent Q state at room temperature via an efficient photochemical process. These variants operate with efficiencies 100 times or more greater than the native protein. One feature of this disclosure is in the efficient use of the branched photocycle architecture of these BR variants in the fabrication of the 3D memory storage device. The photochromic memory architecture of these variants switches between bit 1 and bit 0 states stably for extended periods of time. The genetically optimized BR variants form the permanent Q state with remarkable ease due to their ability to exist in a 9-cis configuration in the dark. Exposure to light causes the cis-trans isomerization, which branches into the alternate photocycle without having to go through the main photocycle as wild-type BR.

In an embodiment, the variants are Q-state forming bacteriorhodopsin variants as set forth below in Table 1.

TABLE 1

| Q State Forming Bacteriorhodopsin Variants | |
|---|---|
| No. | Variant |
| 1 | V49A[a] |
| 2 | V49N[a] |
| 3 | V49P[a] |
| 4 | V49F[a] |
| 5 | T90A |

TABLE 1-continued

Q State Forming Bacteriorhodopsin Variants

| No. | Variant |
|---|---|
| 6 | D85E[a] |
| 7 | R134I |
| 8 | R134A |
| 9 | E194A |
| 10 | E194N |
| 11 | E204Q |
| 12 | E204N |
| 13 | E204G |
| 14 | E204C |
| 15 | L206P |
| 16 | L206R |
| 17 | D85E/D96Q[a] (Husky blue) |
| 18 | D85N/V49A[a] |
| 19 | T90A/V49A[a] |
| 20 | E194C/E204C |
| 21 | E194A/N202I |
| 22 | A196S/F208V |
| 23 | E204G/F208V |
| 24 | D212N/Y185F |
| 25 | I119T/T121S/A126T |
| 26 | T90A/V49A/E204Q[a] |
| 27 | A196S/I198L/P200T/E204A/T205Q/F208V |

[a]Bacteriorhodopsin variants can enter the branched photocycle via a single photon process and/or a two photon process to form the permanent Q state. The remaining variants form the Q state via a two photon process (sequential one photon reaction)

The present disclosure relates to the use of the photochromic materials of these BR variants to provide a non-volatile, rewriteable, readable, and erasable three dimensional memory storage devices. It is the objective herein to provide a protein-based memory architecture that rivals the present day silicon-based memory chips in attributes of high capacity, speed, density, and optical data throughput processing. The branched photocycle design employs a photo optical protein with a stable resting ground state and a series of excited metastable and stable states. Paging a small volume within the photosensitive protein-based memory matrix with red light of known wavelength is used to write information precisely in that specific region of the matrix while avoiding unwanted photochemistry in the unaddressed regions of the matrix. Illumination of specific regions within the memory matrix causes the transformation of the stable resting photochromic substance (bit 0) into a stable branched state (bit 1). The unaddressed regions in the matrix remain in the stable resting state. An optical read cycle reads the binary conditions in the exposed regions of the matrix. This memory design allows for parallel data processing with desired data speed relative to silicon chips. Exposure of the illuminated regions of the memory matrix to blue light results in the erasure of the data. Modern day optical and magnetic storage media are oftentimes bulky, delicate and sensitive to radiation damage. The protein based memory matrix is reusable and extremely eco-friendly. In addition the BR variants exhibit increased thermal, chemical and photochromic stability. A key feature provided herein is the generation of a portable, radiation hardened, waterproof, electromagnetic pulse (EMP)-resistant storage media. The protein-based storage media are lightweight, radiation-hardened and stable with a high cyclicity and quantum-efficiency index. The present disclosure describes a protein variant that is capable of storing large amounts of data ($10^{11}$-$10^{13}$ bits) in a small volume of the memory medium. The low cost to produce protein and fabricate the memory matrix provides the comparative advantage of this technology.

Throughout this document, various publications, patents, and/or patent applications are referenced in order to more fully describe the state of the art to which this composition and methods pertain. The disclosures of these publications, patents, and/or patent applications are herein incorporated by reference in their entireties to the same extent as if each independent publication, patent, and/or patent application was specifically and individually indicated to be incorporated by reference.

We claim:

1. A bacteriorhodopsin protein variant, wherein the variant comprises at least two amino acid substitutions of an *H. salinarum* bacteriorhodopsin protein, wherein the two amino acid substitutions are selected from the group consisting of V49X, T90X, D115, I119X, T121X, A126X, Y185X, A196X, I198X, P200X, N202X, I205X, L206X, F208X, and D212X.

2. The bacteriorhodopsin protein variant of claim 1, wherein at least one of the two the amino acid substitutions comprises a conservatively substituted amino acid.

3. The bacteriorhodopsin protein variant of claim 1, wherein the bacteriorhodopsin protein variant is in a memory storage device.

4. The bacteriorhodopsin protein variant of claim 3, wherein the memory storage device is three-dimensional or holographic.

5. The bacteriorhodopsin protein variant of claim 3 wherein the memory storage device is random access memory.

6. The bacteriorhodopsin protein variant of claim 1, further comprising a third amino acid substitution selected from the group consisting of V49X, R82X, D85X, T90X, D96X, D115X, I119X, T121X, A126X, R134X, Y185X, E194X, A196X, I198X, P200X, N202X, E204X, T205X, L206X, F208X, and D212X.

7. The bacteriorhodopsin protein variant of claim 6, comprising at least four amino acid substitutions.

8. The bacteriorhodopsin protein variant of claim 7, comprising five or more amino acid substitutions.

9. A bacteriorhodopsin protein variant, wherein the variant comprises at least one amino acid substitution of an *H. salinarum* bacteriorhodopsin protein, selected from the group consisting of T90X, D115X, I119X, T121X, A126X, Y185X, A196X, I198X, P200X, N202X, T205X, L206X, F208X, and D212X, and further comprising the amino acid substitution V49X.

10. The bacteriorhodopsin protein variant of claim 9, wherein the amino acid substitution comprises a conservatively substituted amino acid.

11. The bacteriorhodopsin protein variant of claim 1, wherein one of the at least two amino acid substitutions comprises V49X, and wherein the variant further comprises the amino acid substitution is D85X.

12. The bacteriorhodopsin protein variant of claim 11, wherein the V49X substitution is V49A, and wherein the D85X substitution D85N.

13. A bacteriorhodopsin protein variant, wherein the variant comprises at least N202X and E194X amino acid substitutions of an *H. salinarum* bacteriorhodopsin protein.

14. The bacteriorhodopsin protein variant of claim 13, wherein the N202X substitution is N202I, and wherein the E194X substitution is E194A.

15. A bacteriorhodopsin protein variant, wherein the variant comprises at least F208X and E204X amino acid substitutions.

16. The bacteriorhodopsin protein variant of claim 15, wherein the F208X substitution is F208V, and wherein the E204X substitution is E204G.

17. The bacteriorhodopsin protein variant of claim 1, wherein the at least two amino acid substitutions are selected from the group consisting of V49A, V49N, V49I, V49F, T90A, I119T, T121S, A126T, Y185F, A196S, I198L, P200T, N202I, T205Q, L206P, L206R, F208V, and D212N.

* * * * *

SEQUENCE LISTING

```
<160> NUMBER OF SEQ ID NOS: 1

<210> SEQ ID NO 1
<211> LENGTH: 249
<212> TYPE: PRT
<213> ORGANISM: Halobacterium salinarum

<400> SEQUENCE: 1

Gln Ala Gln Ile Thr Gly Arg Pro Glu Trp Ile Trp Leu Ala Leu Gly
1               5                   10                  15

Thr Ala Leu Met Gly Leu Gly Thr Leu Tyr Phe Leu Val Lys Gly Met
            20                  25                  30

Gly Val Ser Asp Pro Asp Ala Lys Lys Phe Tyr Ala Ile Thr Thr Leu
        35                  40                  45

Val Pro Ala Ile Ala Phe Thr Met Tyr Leu Ser Met Leu Leu Gly Tyr
    50                  55                  60

Gly Leu Thr Met Val Pro Phe Gly Gly Glu Gln Asn Pro Ile Tyr Trp
65                  70                  75                  80

Ala Arg Tyr Ala Asp Trp Leu Phe Thr Thr Pro Leu Leu Leu Leu Asp
                85                  90                  95

Leu Ala Leu Leu Val Asp Ala Asp Gln Gly Thr Ile Leu Ala Leu Val
            100                 105                 110

Gly Ala Asp Gly Ile Met Ile Gly Thr Gly Leu Val Gly Ala Leu Thr
```

-continued

|  | 115 |  |  |  | 120 |  |  |  | 125 |  |  |  |
|---|---|---|---|---|---|---|---|---|---|---|---|---|
| Lys | Val | Tyr | Ser | Tyr | Arg | Phe | Val | Trp | Trp | Ala | Ile | Ser | Thr | Ala | Ala |
|  | 130 |  |  |  | 135 |  |  |  | 140 |  |  |  |
| Met | Leu | Tyr | Ile | Leu | Tyr | Val | Leu | Phe | Phe | Gly | Phe | Thr | Ser | Lys | Ala |
| 145 |  |  |  | 150 |  |  |  | 155 |  |  |  | 160 |
| Glu | Ser | Met | Arg | Pro | Glu | Val | Ala | Ser | Thr | Phe | Lys | Val | Leu | Arg | Asn |
|  |  |  | 165 |  |  |  | 170 |  |  |  | 175 |  |
| Val | Thr | Val | Val | Leu | Trp | Ser | Ala | Tyr | Pro | Val | Val | Trp | Leu | Ile | Gly |
|  |  | 180 |  |  |  | 185 |  |  |  | 190 |  |
| Ser | Glu | Gly | Ala | Gly | Ile | Val | Pro | Leu | Asn | Ile | Glu | Thr | Leu | Leu | Phe |
|  | 195 |  |  |  | 200 |  |  |  | 205 |  |  |
| Met | Val | Leu | Asp | Val | Ser | Ala | Lys | Val | Gly | Phe | Gly | Leu | Ile | Leu | Leu |
| 210 |  |  |  | 215 |  |  |  | 220 |  |  |  |
| Arg | Ser | Arg | Ala | Ile | Phe | Gly | Glu | Ala | Glu | Ala | Pro | Glu | Pro | Ser | Ala |
| 225 |  |  |  | 230 |  |  |  | 235 |  |  |  | 240 |
| Gly | Asp | Gly | Ala | Ala | Ala | Thr | Ser | Asp |
|  |  |  | 245 |  |  |